United States Patent
Matthews et al.

(10) Patent No.: US 11,373,311 B2
(45) Date of Patent: Jun. 28, 2022

(54) SYSTEM AND METHODS FOR DETERMINING A BRAIN CONDITION OF A PATIENT SUBJECT TO MULTIPLE DISEASE STATES

(71) Applicant: ADM DIAGNOSTICS, LLC, Skokie, IL (US)

(72) Inventors: Dawn C. Matthews, Grayslake, IL (US); Ana S. Lukic, Chicago, IL (US); Randolph D. Andrews, McHenry, IL (US)

(73) Assignee: ADM DIAGNOSTICS, INC., Northbrook, IL (US)

( * ) Notice: Subject to any disclaimer, the term of this patent is extended or adjusted under 35 U.S.C. 154(b) by 116 days.

(21) Appl. No.: 15/743,380

(22) PCT Filed: Jul. 15, 2016

(86) PCT No.: PCT/US2016/042490
§ 371 (c)(1),
(2) Date: Jan. 10, 2018

(87) PCT Pub. No.: WO2017/011746
PCT Pub. Date: Jan. 19, 2017

(65) Prior Publication Data
US 2018/0204327 A1 Jul. 19, 2018

Related U.S. Application Data

(60) Provisional application No. 62/192,931, filed on Jul. 15, 2015.

(51) Int. Cl.
*G06K 9/00* (2022.01)
*G06T 7/00* (2017.01)
(Continued)

(52) U.S. Cl.
CPC .......... *G06T 7/0016* (2013.01); *A61B 5/0042* (2013.01); *A61B 5/055* (2013.01);
(Continued)

(58) Field of Classification Search
CPC .......... A61B 6/03; A61B 6/52; A61B 6/5205; A61B 6/5211; A61B 6/5217; A61B 8/52;
(Continued)

(56) References Cited

U.S. PATENT DOCUMENTS

| | | | |
|---|---|---|---|
| 2004/0120557 A1* | 6/2004 | Sabol | G09B 23/28 382/128 |
| 2004/0122703 A1* | 6/2004 | Walker | G16H 50/70 705/2 |

(Continued)

OTHER PUBLICATIONS

Deepak, Automated Categorization of Brain Tumor from MRI Using CNN features and SVM, Oct. 2020, Sprinker (Year: 2020).*
(Continued)

*Primary Examiner* — Alex Kok S Liew
(74) *Attorney, Agent, or Firm* — Quarles & Brady LLP

(57) ABSTRACT

System and methods for identifying a brain condition of a patient subject to a plurality of disease states are provided, in some aspects, the method includes receiving imaging data associated with a patient's brain acquired using an imaging system, and constructing a classifier having signatures corresponding to a plurality of disease states. The method also includes applying the classifier to the imaging data to determine a degree to which the patient expresses at least one of the plurality of disease states, and determining a brain condition of the patient using the determined degree. The method further includes generating a report indicative of the brain condition of the patient.

23 Claims, 11 Drawing Sheets

(51) Int. Cl.
*G06K 9/62* (2022.01)
*G06V 20/69* (2022.01)
*G16H 15/00* (2018.01)
*G16H 50/20* (2018.01)
*G16H 30/40* (2018.01)
*A61B 5/00* (2006.01)
*A61B 5/055* (2006.01)
*A61B 6/03* (2006.01)

(52) U.S. Cl.
CPC .......... *A61B 5/4088* (2013.01); *A61B 5/4842* (2013.01); *A61B 5/4848* (2013.01); *A61B 5/7267* (2013.01); *A61B 6/032* (2013.01); *A61B 6/037* (2013.01); *G06K 9/623* (2013.01); *G06K 9/6268* (2013.01); *G06K 9/6293* (2013.01); *G06V 20/698* (2022.01); *G16H 15/00* (2018.01); *G16H 30/40* (2018.01); *G16H 50/20* (2018.01); *G06T 2207/10104* (2013.01); *G06T 2207/20081* (2013.01); *G06T 2207/30016* (2013.01); *G06V 2201/03* (2022.01); *G06V 2201/031* (2022.01)

(58) Field of Classification Search
CPC ... A61B 8/5207; A61B 8/5223; A61B 8/5215; G06T 2207/10088; G06T 7/0012; G06T 2207/30096; G06T 2207/10024; G06T 2207/20036; G06T 7/0014; G06T 2207/20016; G06T 2207/20032; G06T 2207/30041; G06T 2207/30104; G06T 2207/30168; G06T 3/0068; G06T 3/0093; G06T 3/40; G06T 5/008; G06T 5/20; G06T 7/0016; G06T 2207/30068; G06T 7/11; G06T 2207/10056; G06T 2207/30024; G06T 2207/10116; G06T 2207/10132; G06T 2207/30008; G06T 7/136; G06T 7/187; G06T 7/38; G06T 7/45; G06T 7/64; G06T 2207/20064; G06T 2207/20081; G06T 2207/20084; G06T 7/246; G16H 50/20; G16H 30/20; G16H 30/40

See application file for complete search history.

(56) References Cited

U.S. PATENT DOCUMENTS

| | | | | |
|---|---|---|---|---|
| 2004/0122706 | A1* | 6/2004 | Walker | G16H 50/20 705/2 |
| 2004/0122707 | A1* | 6/2004 | Sabol | G07C 9/37 705/2 |
| 2004/0122708 | A1* | 6/2004 | Avinash | G16H 10/20 705/2 |
| 2004/0122709 | A1* | 6/2004 | Avinash | G16H 40/67 705/2 |
| 2008/0101665 | A1* | 5/2008 | Collins | A61B 5/4088 382/128 |
| 2009/0292478 | A1* | 11/2009 | Avinash | G16H 70/60 702/19 |
| 2011/0286650 | A1* | 11/2011 | Roy | A61B 5/4088 382/131 |
| 2012/0053447 | A1* | 3/2012 | Duchesne | A61B 5/055 600/410 |
| 2012/0082362 | A1* | 4/2012 | Diem | G01N 21/31 382/133 |
| 2014/0148657 | A1 | 5/2014 | Hendler | |
| 2014/0155730 | A1* | 6/2014 | Bansal | A61B 5/0476 600/409 |
| 2016/0054409 | A1* | 2/2016 | Wager | A61B 5/055 600/411 |
| 2016/0166229 | A1* | 6/2016 | Matthews | A61B 6/582 600/431 |

OTHER PUBLICATIONS

Yoo, Feasibility study to improve deep learning in OCT diagnosis of rare retinal diseases with few-shot classification, Jan. 2021, Medical & Biological Engineering & Computing (Year: 2021).*
US Patent Office; International Search Report and Written Opinion, dated Oct. 7, 2016.

* cited by examiner

CV1

SYSTEM AND METHODS FOR DETERMINING A BRAIN CONDITION OF A PATIENT SUBJECT TO MULTIPLE DISEASE STATES

CROSS-REFERENCE TO RELATED APPLICATIONS

This application represents the national stage entry of PCT International Application No. PCT/US2016/042490 filed on Jul. 15, 2016 and claims U.S. Provisional Patent Application Ser. No. 62/192,931 filed on Jul. 15, 2016, the contents of which are hereby incorporated by reference as if set forth in their entirety herein.

BACKGROUND

The present disclosure relates generally to systems and methods for determining a medical condition of a patient using imaging data and, in particular, to systems and methods for determining the presence and progression of a brain condition for a patient suffering from, or exhibiting signs of multiple disease states.

Neurodegenerative diseases and other syndromes affecting the brain commonly exhibit distinctive symptoms and characteristics that often become more pronounced as disease severity increases. During diagnosis, specific signatures visible on various imaging modalities are utilized to determine the presence and state of the disease. For instance, as glucose is a primary source of energy for neuronal activity, measurement of glucose metabolism using positron emission tomography ("PET") imaging has been demonstrated to provide a sensitive measure of neuronal activity decline in affected brain areas for a variety of neurodegenerative diseases and syndromes. Other imaging modalities, such as functional MRI, single photon emission computed tomography ("SPECT"), as well as early time frames of amyloid, tau, and others tracer biomarkers, have also been used to measure brain function. Similarly, as neurons degenerate, brain volume also decreases according to characteristic patterns, measurable using magnetic resonance imaging ("MRI"). Additionally, the accumulation of abnormal entities such as amyloid (forming neuritic plaques), tau (forming neurofibrillary tangles), and Lewy Bodies, can be measured using imaging.

For instance, a characteristic pattern for patients suffering from Alzheimer's Disease ("AD") includes glucose hypometabolism emerging in medial temporal cortex and posterior cingulate, expanding to temporo-parietal regions, and gradually affecting most cortical tissue, while the pons, cerebellum, and motor and visual cortices are relatively preserved. Changes are found in genetically at-risk individuals, beginning years before any symptom onset, and correlating with clinical decline. AD also causes structural atrophy that initiates in entorhinal cortex, spreads to hippocampus, and expands to parietal and most cortical and subcortical structures, and correlates with clinical progression.

Neurodegenerative diseases are often co-morbid with other disorders, and signatures exhibited on PET or MRI often reflect their combined effect. For example, a certain percentage of patients with AD also have Lewy Body Disease or vascular dementia. Also, Down Syndrome ("DS") patients has been shown to have neuritic plaques and neurofibrillary tangles in nearly all DS adults over the age 40, consistent with AD patients. Studies in adults also found hypometabolism in AD-relevant regions, more pronounced in demented than non-demented subjects. Also, Alzheimer's-like dementia was shown to be prevalent in up to 55% of DS individuals in their forties, and 77% over age 60. MRI studies of young patients with DS were shown to have reduced brain volume, shortened frontal lobes, reduced cerebellum, brainstem, hippocampus, amygdala, and white matter, and preserved parietal and subcortical regions. In addition, studies in DS adults found lower volumes overall and in cerebellum, cingulate gyrus, frontal lobe, superior temporal lobes and hippocampi, and an association between dementia, regional atrophy typical of AD, and ventricular enlargement.

Neurodegenerative diseases may also coexist with neuropsychiatric conditions, including depression, and certain conditions can increase the risk of the accelerated development of dementias, such as AD. For instance, Traumatic Brain Injury ("TBI"), involving a concussion or other injury, can increase the risk of developing AD. In particular, repeated concussions have been linked to the development of Chronic Traumatic Encephalopathy ("CTE"), a neurodegenerative disease that also involves dementia along with numerous other devastating effects. Furthermore, studies on Parkinson's disease ("PD") have shown that at least one third of patients can develop dementia due to AD or other forms of disease.

Typical methods for identifying and assessing disease progression involve comparing the brains scans of a patient with reference data from prior scans or a known patient group, which is expected to remain relatively stable for each disease type or over time. This includes defining various regions of interest ("ROIs"), such as the posterior cingulate or medial temporal cortex, and performing a comparison between the image data and the reference data associated with the ROIs. In determining disease progression using PET imaging, for instance, the mean signal intensity in each defined ROI is typically divided by the intensity value associated with a reference region, such as whole brain, pons, or cerebellum.

Also, statistical parametric mapping software is often used to compare groups of images from different patients. The images are first spatially transformed so that brain structures are properly aligned, and then compared on a voxel-by-voxel basis using statistical analyses. The result is a set of voxels or clusters of voxels in which statistical differences are found between the groups of images. However, as described, neurodegenerative diseases are often co-morbid with other disorders, and brain images capture the composite effect of all such neurodegenerative, congenital, neuropsychiatric, or other influences acting on the brain. Therefore, measuring a region, or comparing two groups of scans, reveals only the combined effects of all contributing influences, distorting or confounding results for specific diseases or conditions.

Attempts to separate the effects of different diseases or syndromes within the same subject typically have involved, for instance, identifying a group of patients having a first disease, a group having a second disease, and/or a group with both. Images from each group are then compared to determine signatures associated with the first disease, the second disease, and the combination. Since subjects in each group are different, an assumption is made that specific diseases affect subjects in the same way. However, this approach does not identify the contribution of each disease within the same subject, and does not identify the extent to which each patient is expressing one disease versus another. Also, this approach does not allow tracking of individual disease progression. Similar comparative methods have also involved non-imaging measurements, comparing measurements obtained from different disease groups and normal controls.

As a step beyond traditional region of interest or statistical parametric mapping approaches, multivariate machine learning methods have also been applied to image data to identify patterns of affected brain regions or other parameters associated with disease. These methods take advantage of the relationships, or correlations, between affected regions. In some approaches, feature reduction methods, such as such as principal component analysis ("PCA"), are applied to extract meaningful signal from background noise. Example algorithmic approaches include Canonical Variate Analysis ("CVA"), Support Vector Machines ("SVM"), Relevance Vector Machines ("RVM"), and other models. However, the application of machine learning methods and other classification techniques has focused on identifying the presence of a specific disorder within a patient. For instance, typical discrimination algorithms are used to match a patient to specific diagnostic classes such as, for example, AD, DS, Fronto-Temporal Dementia ("FTD"), and so forth.

As may be appreciated from the above, the ability to differentiate co-morbid diseases in a patient can be critical to the proper diagnosis and treatment. Such differentiation may also be essential in order to conduct informative pharmaceutical clinical trials in co-morbid populations. For example, there is pharmaceutical company interest in the recruitment of DS subjects, due to their accelerated incidence and high prevalence of AD, to provide an enriched population in which to evaluate AD-targeted drugs. Hence, disassociation of contributions of DS from those of AD is highly advantageous in order to initiate therapy at a well-characterized point in AD development and identify treatment specific to AD. Also, the ability for predicting which PD patients are on a path to developing dementia is highly desirable, since such prediction could enable preventative or early stage treatment. This would require dissociating effects of PD from those indicative of emerging AD or other dementias, which is not possible using present technologies. Furthermore, among athletes, military personnel, veterans and others impacted by brain trauma, there is a strong desire to identify who may be progressing on a path toward dementia, and of what type, enabling intervention and/or proper treatment.

Therefore, given the above, there is a need for systems and methods capable of separating the relative contributions of different co-morbid disease states in order to properly diagnose and treat patients.

SUMMARY

The present disclosure overcomes the drawbacks of aforementioned technologies by providing systems and methods for identifying the brain condition of a patient subject to a plurality of disease states. In particular, the present disclosure describes an approach for separating, using the imaging data, signatures associated with different disease states in order to determine the presence and progression of at least one of the disease states. In some aspects, a machine learning approach and pre-defined comparator classes may be utilized to dissociate and quantify the expression of two or more different diseases or syndromes within the same set of scans. For example, the effects on Positron Emission tomography ("PET") imaging due to Down Syndrome ("DS") may be separated from those of Alzheimer's Disease ("AD").

As will be appreciated from descriptions herein, the present approach is advantageous in properly diagnosing and treating patients suffering from, or exhibiting signs of multiple diseases or syndromes. In this manner, different disease states may be independently tracked over time and correlated with clinical outcomes. In addition, patients suitable for specific clinical trials may be more accurately identified.

In accordance with one aspect of the disclosure, a method for identifying a brain condition of a patient subject to a plurality of disease states is provided. The method includes receiving imaging data associated with a patient's brain acquired using an imaging system, and constructing a classifier having signatures corresponding to a plurality of disease states. The method also includes applying the classifier to the imaging data to determine a degree to which the patient expresses at least one of the plurality of disease states, and determining a brain condition of the patient using the determined degree. The method further includes generating a report indicative of the brain condition of the patient.

In accordance with another aspect of the disclosure, a method for identifying a brain condition of a patient subject to a plurality of disease states is provided. The method includes acquiring imaging data associated with a patient's brain, and applying a classifier to the imaging data to determine a degree to which the patient expresses at least one of the plurality of disease states. The method also includes separating the imaging data using the determined degree to produce datasets corresponding to the at least one of the plurality of disease states, and determining a brain condition of the patient using respective datasets. The method further includes generating a report indicative of the brain condition of the patient.

In accordance with yet another aspect of the disclosure, a system for identifying a brain condition of a patient subject to a plurality of disease states is provided. The system includes an input configured to receive imaging data associated with a patient's brain, and at least one processor configured to construct a classifier having signatures corresponding to a plurality of disease states, and apply the classifier to the imaging data to determine a degree to which the patient expresses at least one of the plurality of disease states. The processor is also configured to determine a brain condition of the patient using the determined degree, and generate a report indicative of the brain condition of the patient. The system further includes an output configured to provide the report to a user.

In accordance with yet another aspect of the disclosure, a method for generating a classifier to identify a brain condition of a patient subject to a plurality of disease states is provided. The method includes accessing data parameters acquired from a plurality of patient groups, and assembling the data parameters into a plurality of disease state classes and disease state sub-classes. The method also includes generating, using plurality of disease state classes and disease state sub-classes, a classifier having signatures distinguishing the plurality of disease states, and providing the classifier as a reference for identifying a brain condition of a patient subject to at least one of the plurality of disease states.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present disclosure introduces a novel approach for identifying brain conditions of patients at risk for or suffering from multiple diseases or syndromes. In particular, using a novel classifier, contributions of various disease states to a patient's data can be disassociated. This allows direct evaluation of the degree to which each disease state is expressed in the data, as well as the tracking of progression (or treatment-related modification) separately. Specifically, the classifier described herein includes several unique features, including the way in which classes are defined, the iterative re-sampling approach that is used to optimize the discriminant pattern definition, and other technical aspects associated with the machine learning algorithm utilized. Further, the classifier is indifferent to whether the inputted data is in the form of image voxels or other parameters, such as cognitive or laboratory measures, genes, single nucleotide polymorphisms, or other variables. Therefore, the present approach may utilize a variety of data types.

Figure 1:
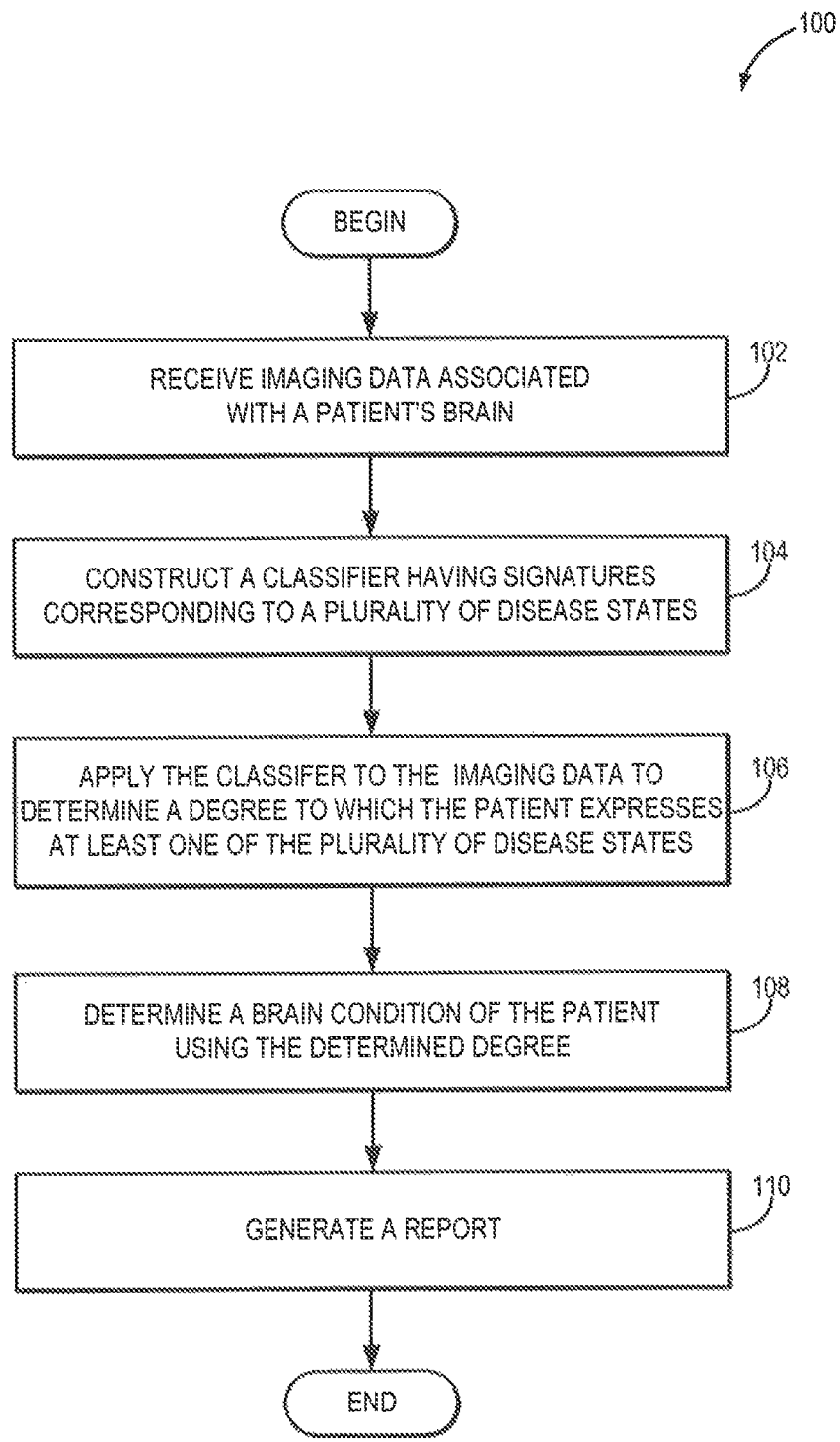
FIG. 1 is a flowchart setting forth the steps of a process in accordance with aspects of the present disclosure.

Referring now to FIG. 1, steps of a process 100 in accordance with aspects of the present disclosure are shown. In some implementations, the process 100 may be carried out using a system 400 as described with reference to FIG. 4, or alternatively another suitable system. In particular, the process 100 may begin at process block 102 whereby imaging data, as well as other data acquired from a patient subject to one or more disease states, may be received or accessed from a data storage, memory, or an imaging system. In one example, a patient may be suffering from Down Syndrome ("DS") and have an indication of Alzheimer's Disease ("AD"). In another example, a patient may be suffering from Parkinson's Disease ("PD") with a degree of cognitive impairment (or a homogenous level of impairment). In yet another example, a patient may have experienced traumatic brain injury ("TBI"), and be at risk or in the process of developing AD.

In some aspects, imaging data may be acquired at process block 102 using a Positron Emission Tomography ("PET") system, a Computed Tomography ("CT") system, a Magnetic Resonance Imaging ("MRI") system, a Single Photon Emission Computed Tomography ("SPECT") system, or other imaging system. However, other data types may also be obtained from the patient at process block 102. For example, cognitive and functional test scores, genotype, Cerebrospinal Fluid ("CSF") levels, e.g. Abeta42, Total tau, p-tau alpha-synuclein, blood based biomarkers, other test scores, e.g. sense of smell, amyloid content in eye, and so forth.

At process block 104, a classifier may then be constructed, the classifier including therein various patterns or signatures associated with different disease states potentially affecting the patient. The classifier may be constructed using a machine learning algorithm, although other techniques may also be utilized. In constructing the classifier, data or parameters from various patient groups expressing different or various syndromes or diseases, as well as normal controls, may be utilized. In one implementation, comparator data sets may include a normal control group, a group having a first disease state, and a group having a second disease state, or alternatively, two out of three of those categories. By way of example, in discriminating the effects of DS from those of AD, the following comparator patient categories may be utilized (a) cognitively Normal subjects without DS and without evidence of AD pathology (NL); (b) subjects confirmed to have AD dementia, with AD pathology (amyloid plaque) (AD); and pure DS subjects. As another example, in discriminating the effects of PD from those of AD, the classes could be NL, AD, and PD (PD subjects who may or may not have co-morbid emerging AD), and/or an additional class of PD subjects known not to have AD pathology (amyloid negative). As yet another example, in the case of TBI, the classes could be NL, AD, and TBI, and/or an additional class of TBI subjects known not to have amyloid pathology. It may be readily appreciated that these are non-limiting examples, and therefore a wide variety of patient group data may be utilized to construct the classifier 104.

In training the classifier at process block 104, reference data or parameters associated with different patient groups may be provided, or retrieved from a memory, database, or data storage for analysis. In some aspects, a user may select or define classes to be used in constructing the classifier, depending upon the patient(s) to be analyzed using the classifier. For example, in the case of the DS patients, the classifier may include imaging data from three training classes, namely NL, AD, and DS. In some aspects, canonical variates describing the variance across classes may also be identified. In this example, by having a NL set and an AD set, a pattern differentiating DS subjects from either of the two other classes (NL and AD) may be extracted, as well as a pattern that differentiates NL from AD. In the case that 18-F Fluorodeoxyglucose ("FDG") PET imaging data is utilized, such patterns may indicate relative glucose hypo- and hyper-metabolism that when mathematically combined describe the total variance across the groups. As an alternative, or complement, amyloid PET, tau PET may also be used to measure the accumulation of pathological entities such as the amyloid plaques and tangles, which are hallmarks of AD. Furthermore, other imaging modalities may also be utilized, including structural MRI data, with signatures or patterns indicating differences in tissue volume, including tissue atrophy, that when mathematically combined describe the total variance across the groups.

In addition to classes being associated with different disease states, the constructed classifier may also include various sub-classes for one or more disease states. For instance, the classifier may include patterns corresponding to Mild Cognitive Impairment ("MCI"), later stage MCI, and so forth. Furthermore, classes associated with other characteristic signatures or patterns may be used. For instance, as mentioned, relative volume atrophy (or deficit), as well as preservation (or increase) as discerned using structural MRI, for instance, may be utilized to determine a brain condition of a patient. Also, functional measures and cognitive measures, which can be specific to particular domains such as short term memory, long term memory, or executive function, may also be used to characterize and distinguish various disease states. Fluid biomarkers including cerebrospinal fluid levels of Abeta42, tau, and other entities, and blood levels of various proteins, provide additional defining characteristics of disease. Genotype information, demographics, and other parameters provide yet additional covariates and may aid in disease identification and discrimination. Therefore, it may be appreciated that any number and types of subject classes, based on various data and parameters from various patient groups, may be included in constructing the classifier.

At process block 106, the constructed classifier may then be applied to the imaging data, and other data, obtained from the patient to determine a degree to which the patient expresses different disease states. In addition, each pattern may be associated with a canonical variate score, which quantifies the degree to which each subject expressed the particular pattern. In some aspects, applying the classifier may include comparing the imaging data associated with selected regions of interest ("ROIs") to signatures or patterns associated with each of the different disease states to determine the degree to which the patient expresses at least one of the disease states. A classification confidence for the degree to which the patient expresses the disease states may also be computed at process block 106.

Figure 2A:
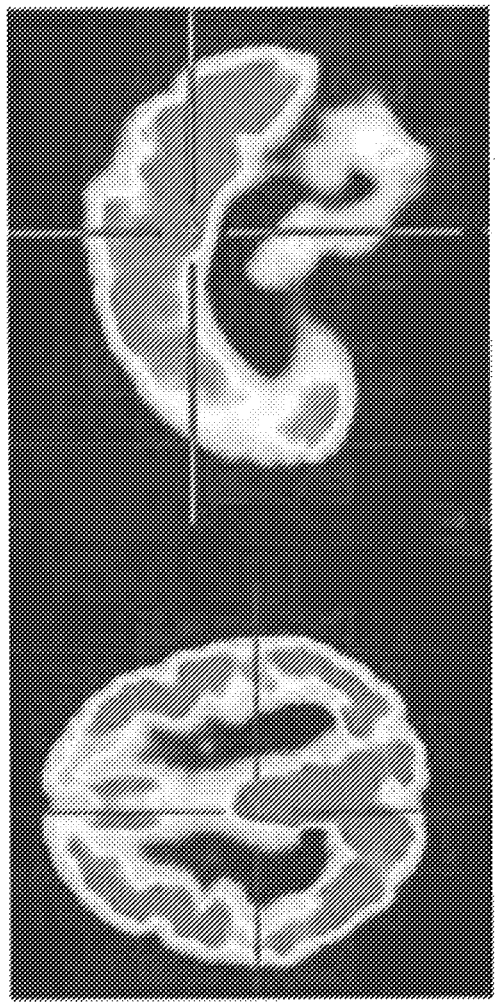
FIG. 2A shows example axial and sagittal 18-F Fluorodeoxyglucose ("FDG") Positron Emission Tomography ("PET") images for a normal patient.
Figure 2B:
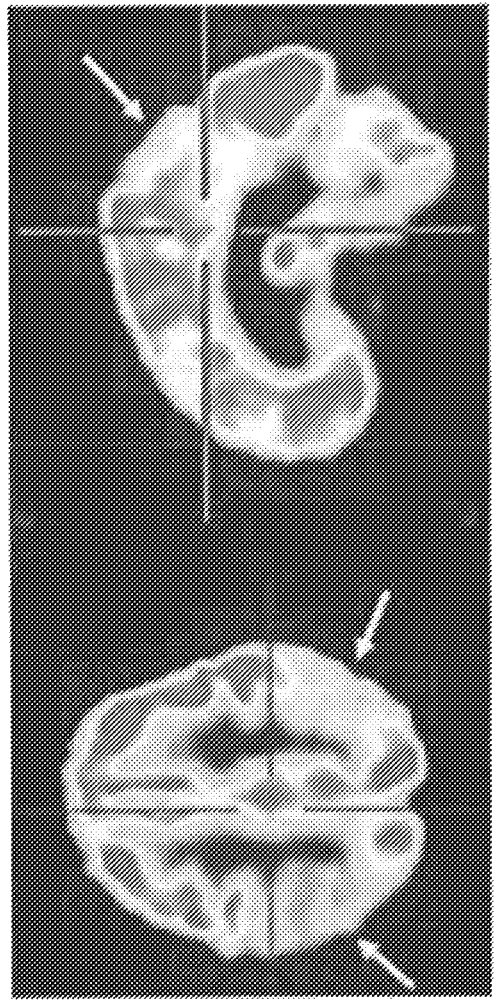
FIG. 2B shows an example pattern of hypometabolism in axial and sagittal one FDG PET images for a patient with Alzheimer's Disease ("AD").

By way of example, FIGS. 2A-B illustrates patterns of metabolism of a normal patient (FIG. 2A) compared to a patient with AD (FIG. 2B) as viewed on axial and sagittal FDG PET images. As may be appreciated from the figures, neuronal activity in patients with AD is reduced in certain brain regions, even very early in disease, gradually expanding to include much of the brain and with pronounced loss in the posterior cingulated, precuneus, and inferior parietal regions, as indicated by arrows in FIG. 2B. Such characteristic disease patterns may be utilized in determining a brain condition of a patient. For instance, in disassociating the effects of DS and AD, for example, characteristic patterns of relative hypo- and hyper-metabolism as discerned on FDG PET imaging may be utilized.

In some implementations, imaging data and other data may be separated at process block 106, according to the degree to which the patient expresses each disease state, to produce datasets that can be analyzed, and optionally displayed, separately. As such, each produced dataset may include data representative of a disease state that is disassociated from other, co-morbid, disease states. Using such datasets, the extent to which a subject expresses a certain pattern, such as a DS pattern for example, can be characterized or monitored separately from the extent to which they express a different pattern, such as an AD-like pattern for example.

A brain condition of the patient may then be determined using the degree to which the patient expresses one or more disease states, as indicated by process block 108. In determining the brain condition, a reference or database may be used, the reference including various information correlating various disease states, and degree of expression with various brain conditions, as well as other information. In determining the brain condition, information specific to the patient may also be used, such as age, gender, medical condition, physiological parameters, and so forth. In some aspects, the determined brain condition may then be utilized to identify, for instance, a disease progression, or an effectiveness of an administered medication or treatment. To this end, the brain condition may be tracked over a period of time. In other aspects, the determined brain condition may be used to identify a future disease state or a risk for developing a future disease state. As such, baseline or reference data or information previously acquired from the patient, or a patient population, may be utilized.

A report may then be generated, as indicated by process block 110, the report being provided to a user via an output, such as a display. In some aspects, the report may indicate a degree to which the patient expresses one or more disease states, the presence and/or progression of the brain condition, a projected clinical outcome, a rate of clinical worsening, and so forth. The report may also include a classification confidence or accuracy for the degree to which the patient expresses the disease states.

Figure 3:
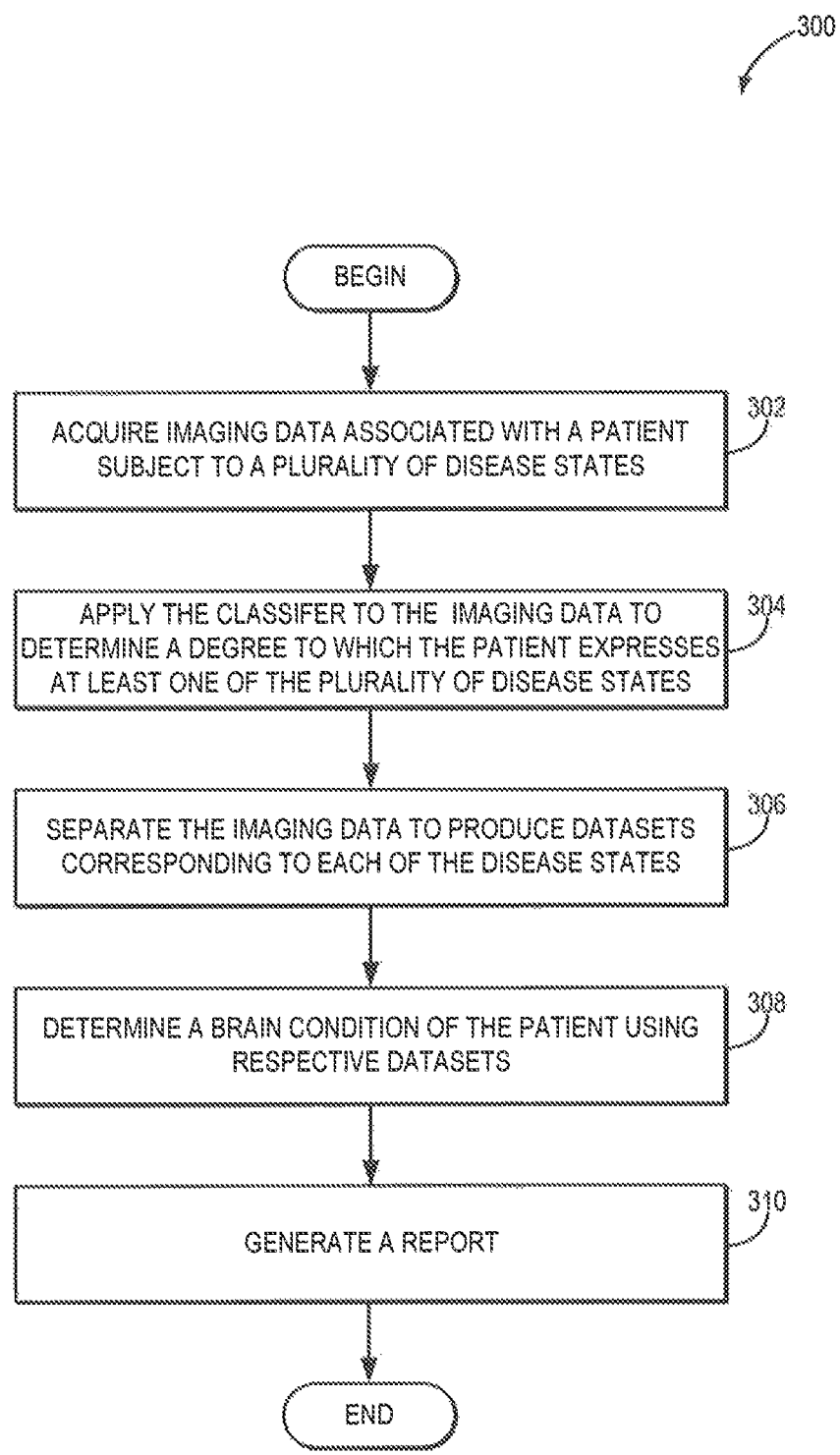
FIG. 3 is another flowchart setting forth the steps of a process in accordance with aspects of the present disclosure.

Referring now to FIG. 3, steps of another process 300 in accordance with aspects of the present disclosure are shown. In some implementations, the process 300 may be carried out using a system 400 as described with reference to FIG. 4, or alternatively another suitable system. The process 300 may begin at process block 302 where imaging data, and other data, associated with a patient subject to a plurality of disease states is acquired. At process block 304, a classifier may then be applied to the imaging data to determine a degree to which the patient expresses at least one of the disease states. The classifier may be constructed at process block 304, as described, for instance using a machine learning algorithm, or may be retrieved or accessed from a memory, database, or other storage medium. As mentioned, the classifier may include signatures, and other information, indicative of various disease states.

At process block 306, the imaging data, and other data, may be separated to produce datasets corresponding to each of the expressed disease states, in accordance with the determined degree. A brain condition of the patient may then be determined using respective datasets, and a report is generated, as indicated by process block 308 and 310, respectively. As described, the report may indicate a degree to which the patient expresses one or more disease states, the presence and/or progression of the brain condition, a projected clinical outcome, a rate of clinical worsening, and so forth.

Figure 4:
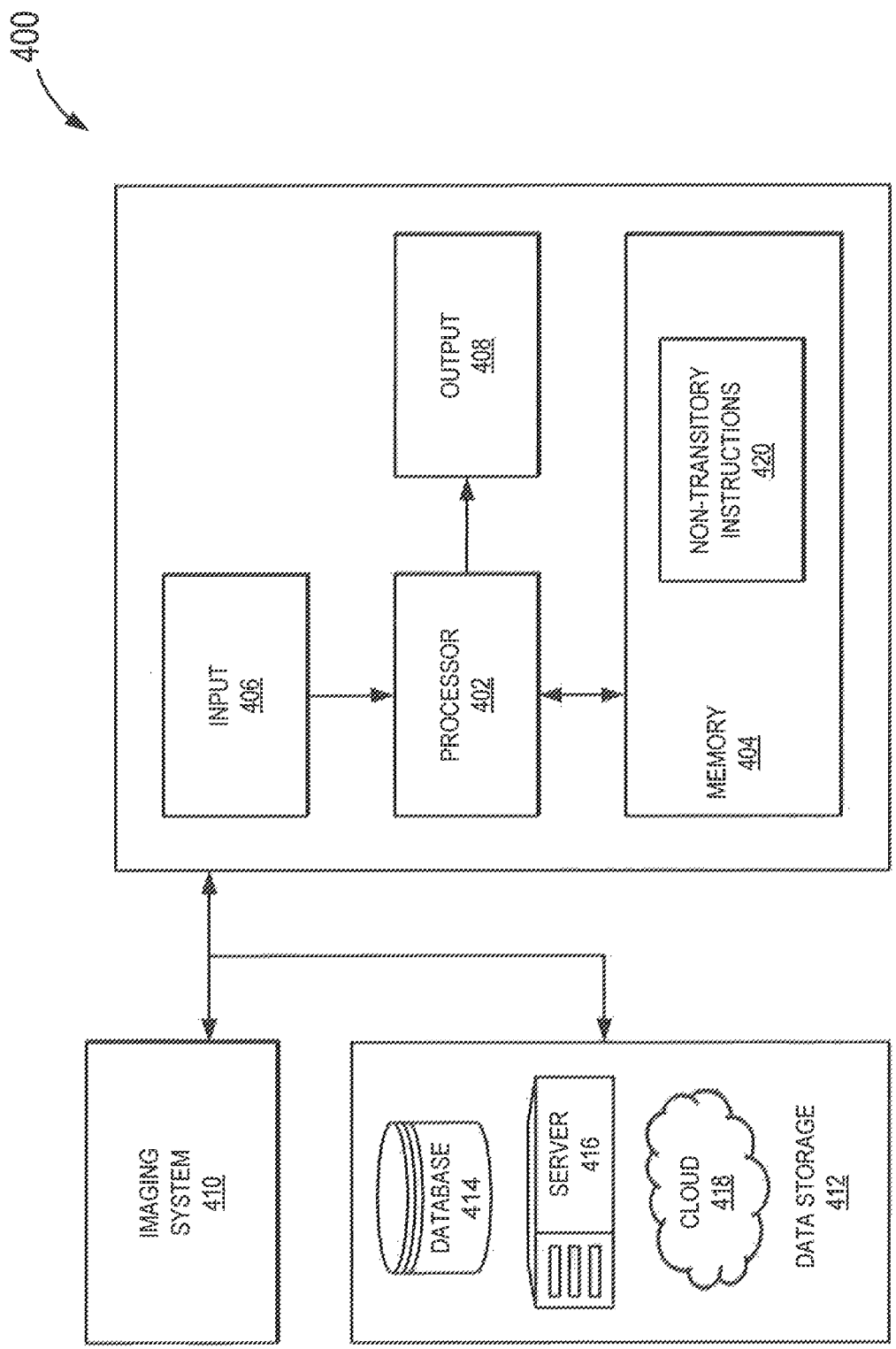
FIG. 4 is a diagram of a system in accordance with aspects of the present disclosure.

Turning now to FIG. 4, a block diagram of a system 400 in accordance with aspects of the present disclosure is shown. In some configurations, the system 400 can include a processor 402, a memory 404, an input 406, an output 408, and may be configured to carry out steps, in accordance with methods described herein, including identifying a brain condition of a patient subject to a plurality of disease states using imaging data, and other data.

In general, the system 400 may be any device, apparatus or system configured for carrying out instructions for, and may operate as part of, or in collaboration with a computer, system, device, machine, mainframe, or server. In this regard, the system 400 may be a system that is designed to integrate with a variety of software and hardware capabilities and functionalities, and may be capable of operating autonomously. In some aspects, the system 400 may be portable, such as a mobile device, tablet, or other portable device or apparatus.

As shown in FIG. 4, in some implementations, the system 400 may be in communication with an imaging system 410 allowing access to imaging, and other information obtained from one or more patients, via input 406 by way of wired or wireless connection. For example, the imaging system 410 may include Positron Emission Tomography ("PET") system, a Computed Tomography ("CT") system, a Magnetic Resonance Imaging ("MRI") system, a Single Photon Emission Computed Tomography ("SPECT") system, and the like. The system 400 may also be in communication with an external data storage 412 that may include a database 414, a server 416, or a cloud 418, and so forth. In some configurations, the input 406 may also include a flash-drive, a USB, a CD/DVD drive, or other input device configured for accessing/retrieving computer-readable media, as well as other functionalities. In this manner, imaging data, such as PET and MRI data, as well as other data, may be retrieved and processed, in accordance with aspects of the disclosure. Non-limiting examples of other data include performance data, cognitive and functional test scores, genotype, Cerebrospinal Fluid ("CSF") levels, e.g. Abeta42, Total tau, p-tau alpha-synuclein, blood based biomarkers, other test scores, e.g. sense of smell, amyloid content in eye, and so forth, as well as patient characteristics, medical history, and so forth. In addition, in some aspects, the input 406 may also be in the form of a mouse, keyboard, touch screen or other device capable of receiving user input. Non-limiting example user input may include selection of operational modes and parameters, regions of interest, classes for constructing a classifier, and others, in accordance with aspects of the present disclosure.

In addition to being configured to carry out steps for operating the system 400 using instructions stored in the memory 404, the processor 402 may also be configured to receive, access and process imaging data, and other data, in accordance with aspects of the present disclosure. Specifically, as shown in FIG. 4, the processor 402 may execute non-transitory instructions 420, stored in memory 404 in the form of non-transitory computer-readable media. In some aspects, the processor 402 may be configured to construct a classifier using accessed or retrieved data in order to produce various signatures or patterns corresponding to different disease states, as described. Example disease states can include DS, AD, PD, TBI, depression, and others. As described, signatures may include glucose metabolism patterns associated with specific ROIs in the brain, as well as other signatures. In particular, the processor 402 may process data from various patient groups in order to construct the classifier, the data being retrieved from the external data storage 412, the imaging system 410, the memory 404, or other location. In some aspects, the processor 402 may be configured to apply machine learning algorithm to construct the classifier. To this end, the processor 402 carry out a number of processing steps, as detailed below. Alternatively, the processor 402 may access a classifier stored in memory 404, data storage 412, or another storage location.

The processor 402 may also be configured to apply the constructed or accessed classifier to imaging data, and other data obtained from a patient, to determine a degree to which the patient expresses various disease states. The processor 402 may also compute a classification confidence or accuracy for the degree to which the patient expresses various disease states. Using the degree of expression of various disease states, the processor 402 may determine a brain condition of a patient, a severity of a brain condition, or a change in brain condition. In some aspects, the processor 402 may utilize the determined degree to separate the data, including imaging data, obtained from the patient in order to disassociate contributions from individual disease states. Specifically, the processor 402 may produce different datasets each corresponding to an expressed disease state. The produced datasets may then be used by the processor 402 to identify and track individual disease states over time, as well as correlate individual disease state with clinical outcomes.

In some aspects, processor 402 may be configured to determine a risk for the patient to develop a disease state using the determined brain condition. The processor may also be configured to determine an effectiveness of a treatment, or a progression of the brain condition using baseline or reference data acquired previously. The processor 402 may be further configured to generate a report provided via output 408. As described, the report may include a variety of information, including a determined brain condition, a degree to which the patient expresses one or more disease states, the presence and/or progression of the brain condition, a projected clinical outcome, a rate of clinical worsening, and so forth.

In another implementation, a method in accordance with aspects of the present disclosure is provided. The method includes obtaining or acquiring image data from a number of individual types. By way of example, a first set of images may be associated with cognitively and pathologically normal patients, a second set may include patients with a known disorder, such as a neurodegenerative, neuropsychiatric, or otherwise abnormal condition, and a third set may include patients with another known disorder that has not been characterized with regard to signature. In some aspects, a portion or all patients in the third set have the same disease or disorder as the second set in varying degrees. In general, any number of image sets corresponding to different disease states may be obtained.

Using the images obtained, a number of image processing techniques may be applied to any or all images. For instance, the images may be geometrically transformed to achieve a specific spatial orientation and dimensions. The images may also be warped onto the same template brain map—allowing respective anatomical regions to spatially overlap for comparison. Alternatively, pre-defined regions of interest may be utilized instead of entire images, such as, for example, hippocampus, posterior cingulate, frontal cortex, pons, cerebellum, and so forth. In some aspects, images may be smoothed to compensate for differences in acquisition conditions, such as scanner resolution. Also, image intensities may be normalized, for instance, by dividing by an average, or other mathematically computed value associated with a particular reference region, or each voxel z-scored to the subject image mean value. In some aspects, an image mean may optionally be removed from each image, or similarly an image group mean may be optionally removed from each image. Other noise filtering approaches may be applied to the images.

Processed images may then be analyzed to derive patterns that explain the variance across the subjects. In some implementations, images may undergo an image decomposition or "feature reduction" through a process such as Principal Component Analysis ("PCA"). This approach finds a set of patterns ("PCs") that when combined account for all variance across subjects. The degree to which a subject expresses each pattern is associated with a numeric score, or PC score. This helps to extract patterns that describe an actual signal of interest and to differentiate from those that capture noise related variability (such as inter-subject differences that do not pertain to disease, or technical signal variability due to different scanners) Patterns that best describe the data of interest can then be selected.

Generated PCs may be mathematically combined into Canonical Variates ("CVs"), which are also patterns that account for the variance across subjects. An optimal number of PCs that represent the signal of interest and help to eliminate unwanted/noisy signal may be selected as the "ingredients" for the CV analysis ("CVA"). Note that CVA is one approach, but other approaches to identify patterns of data include Support Vector Machines ("SVM"), Relevance Vector Machines ("RVM"), nonlinear approaches (e.g. Quadratic), and Partial Least Squares ("PLS"). Feature reduction using PCA may or may not be applied.

A mathematical process to determine a numeric score for each subject in the data set associated with each pattern may be applied. This may be accomplished in the case of whole-image comparison by multiplying the intensities (and direction, positive or negative) against each CV pattern, and summing the product of the intensity of the subject scan and the intensity of the CV pattern in each voxel to create a total score. Alternatively, other mathematical approaches can be used to compare a subject's scan to the CV pattern, or if discrete variables are used, to compare the subject's variables to the CV pattern of variables.

In some aspects, a mathematical process can be optionally applied to increase the robustness of the classifier, in which the training set of N different groups of subjects is repeatedly divided into training halves and test halves. Other ways of splitting the data can also be used. Specifically, one portion of the data may be used to generate the training patterns, and the other portion may be tested as an independent test set against the training patterns. The correlation between the portions may be used to generate a metric of reproducibility. The classification accuracy of selecting the proper group for each subject may be used to generate a prediction metric. Also, the reproducibility and/or prediction metrics may be used to optimize the number of principal components used and other parameters, and to finalize the set of patterns.

In this manner, a number of signature images may be generated. As described, image data from independent subjects may be compared against generated signature images in order to determine their respective brain conditions, clinical prognosis, and so forth. In particular, such signature images may be representative of differences between normal patients and patients suffering from one or more other disease states, in various combinations. For example, when comparing DS AD, and normal patients using an analysis of FDG PET images, generated signature images may be representative of a difference between AD and normal patients. In addition, signature images may also be representative of a difference between DS and both NL and AD patients. As may be appreciated, such approach would not be possible using conventional comparison techniques. In some aspects, the degree to which each subject expresses each distinct pattern may be quantified, for instance, using CV scores.

As another example, signature images representing differences between one or more other disease states may also be generated by analyzing MRI images. For example, one signature may represent a difference between a first disease state or cognitive condition, such as DS, and two other disease states, but may also distinguish, in full or in part, a second and third disease state, such as NL and AD. Another signature may then distinguish the second and third condition (NL and AD), such that it is the combination of scores for these patterns that best distinguishes NL and AD. These scores may be utilized to track the disorders separately. Yet another permutation may include using data from NL, AD, and DS patients with mixed AD progression, using data from DS patients who do not have amyloid, NL, and AD, or else DS patients who do not have amyloid, DS patients who do have amyloid, DS patients who have amyloid and dementia, and AD to obtain at these various patterns. This approach enables extraction important information without need for knowing the amyloid status.

The above approach may be applied to a number of imaging modalities including measurement of glucose metabolism with FDG PET, measurement of amyloid burden and/or blood flow (in early frames) with amyloid PET, measurement of tau burden with tau PET, other PET tracers, measurement of brain structure (and atrophy) with structural MRI, measurement of blood flow with Arterial Spin Labeling ("ASL") MRI, measurement of neuronal activation using BOLD ("Blood Oxygenation Level Dependent") MRI, or Functional MRI (fMRI)—with or without an activation task used, Single Photon Emission Tomography ("SPECT"), or other imaging modalities. As described, the present approach may also implement a number of other data types including cognitive and functional test scores, genotype, blood-based biomarkers, and others.

Non-limiting examples of disease states include Alzheimer's Disease ("AD") and variants, such as Posterior Cortical Atrophy ("PCA") Logopenic Progressive Aphasia ("LPA"), Early Onset AD, Autosomal Dominant AD, Down's Syndrome ("DS"), Traumatic Brian Injury ("TBI"), Chronic Traumatic Encephalopathy ("CTE"), Post-Traumatic Stress Disorder ("PTSD"), depression, hypothyroidism, Psychosis, Lewy Body Disease, vascular disease, Parkinson's disease ("PD"), Parkinson's disease with dementia ("PDD"), Frontotemporal Dementia ("FTD"), including Frontal variant, Semantic dementia ("SD"), Nonfluent Progressive Aphasia ("NFPA"), Corticobasal Syndrome ("CBS"), Prion Disease, Creutzfeldt-Jakob Disease ("vCJD"), Huntingtons Disease ("HD"), motor neuron disease, Amyotrophic Lateral Sclerosis ("ALS"), Normal Pressure Hydrocephalus ("NPH"), Multiple Sclerosis ("MS"), Alcoholism, Wernicke-Korsakoff syndrome, narcotic syndromes, and other diseases, syndromes or deficiencies, including vitamin related, sleep deprivation deficiencies, as well as various combinations thereof.

As may be appreciated from descriptions here, the present approach may be advantageously applied to identify disease state co-morbidities and to (a) discover "pure" patterns using "messy" or at least partially co-morbid data sets whose subjects may have a known disease and a disease or disorder whose characteristics have not yet been defined, (b) enable tracking of those dissociated patterns, and (c) identify the degree to which subject expresses each syndrome or disease separately.

In some implementations, it may be advantageous to resolve disease contributions in pairs or triplets. That is, if a subject appears to have strongest indications of AD and LBD, for example, based upon a multi-class comparison, then further comparison using a NL, AD, LBD classifier, for example, may be performed to determine where they score on each of the disease specific signatures for those primary drivers. Another approach is to obtain subjects with known relative contributions of pathology, for instance as determined from autopsy, and generate a spectrum of classes with varying contributions to find the best match.

The above-described systems and methods may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example I

Down Syndrome ("DS") is associated with an increased rate of Alzheimer's-like dementia, prevalent in up to 55% in individuals in their forties and 77% over age 60. Neuritic plaques and neurofibrillary tangles consistent with Alzheimer's disease ("AD") have been identified in nearly all DS adults examined over age 40. Because of this, DS adults may provide a naturally enriched population in which to evaluate the potential of pharmacological candidates to prevent AD progression. Ideally, trials would initiate treatment at a common, well-defined point prior to AD dementia. This would require characterization within each subject of the degree of AD-related pathology and neurodegeneration distinct from the effects of DS. Detection of disease-modifying effects would require distinguishing treatment impact on AD-related pathology from that on underlying DS.

The present work was directed to dissociating, within DS subjects, signature effects attributable to DS vs. those associated with AD, and to quantifying the degree of AD progression. To achieve this, baseline 18-F fluorodeoxyglucose (FDG) PET imaging and structural MRI biomarkers were analyzed, and relationships with amyloid burden and clinical endpoints were examined. It was hypothesized that non-demented DS subjects with emerging AD would exhibit a pattern of neurodegeneration characteristic of subjects with prodromal AD. It was also postulated that standard methods of image analysis could not fully dissociate effects attributable to DS vs. AD within subjects, and that application of advanced multivariate methods capable of identifying different networks, or contributing patterns to overall effect, could enable isolation of DS and AD components.

In AD, a characteristic pattern of glucose hypometabolism emerges in medial temporal cortex and posterior cingulate, expands to temporo-parietal regions, and gradually affects most cortical tissue while pons, cerebellum, and motor and visual cortices are relatively preserved. Changes are found in genetically at-risk individuals, begin years before symptom onset, and correlate with clinical decline. In DS, FDG PET studies have yielded mixed results. Some studies in young adults (<25 years) have found no differences or only hypermetabolism compared to normals. Studies in DS adults have found hypometabolism in AD-relevant regions, more pronounced in demented than non-demented subjects. Findings have not dissociated the impact of DS from the effects of AD within-subject, nor quantified the degree of AD progression.

AD also causes structural atrophy that initiates in entorhinal cortex, spreads to hippocampus, and expands to parietal and most cortical and subcortical structures, and that correlates with clinical progression. In young persons with DS (ages 5 to 23) MRI studies have shown reduced brain volume, shortened frontal lobes, reductions in cerebellum and brainstem, hippocampus, amygdala, and white matter, and preservation of parietal and subcortical regions. Studies in DS adults have found lower volumes overall and in cerebellum, cingulate gyrus, frontal lobe, superior temporal lobes, and hippocampi, and association between dementia, regional atrophy typical of AD, and ventricular enlargement. However, the structural effects of DS have not been dissociated within-subject from those attributable to AD. Consistent with post-mortem findings, amyloid imaging studies in DS adults have found a high prevalence of AD-like amyloid associated with age and dementia.

The present work builds upon these findings by differentiating, at the subject level, the effects attributable to DS from those associated with emerging AD, and further, provides a quantitative measure of the degree of AD progression. Herein, it is also demonstrated that these measures correlate with amyloid status and clinical endpoints at baseline.

TABLE 1

| Subject demographics. | | | | | | |
|---|---|---|---|---|---|---|
| | DS | NL | EMCI | LMCI | AD | AE-NL |
| Number | 12 | 12 | 12 | 12 | 12 | 12 |
| Age (Mean (S.D.)) | 45 (8.5) | 63 (2.5) | 67 (2.1) | 57 (3.2) | 58 (2.5) | 45 (8.5) |
| Gender (% F) | 83% | 67% | 33% | 42% | 58% | 75% |
| Education (yrs) | 13 (5.1) | 17 (2.0) | 15 (2.6) | 17 (2.5) | 16 (2.7) | n/a |
| ApoE e4 carrier % | 50% | 17% | 92% | 67% | 67% | n/a |
| Amyloid pos | 58%* | 0% | 100% | 100% | 100% | 0% |

TABLE 1-continued

Subject demographics.

Vineland Measures for DS Subjects (adjusted to mental, rather than chronological, age

| | | | |
|---|---|---|---|
| Receptive | 12.58 (3.65) | Expressive | 12.83 (3.74) |
| Written | 15.73 (5.00) | Personal | 14.58 (4.08) |
| Domestic | 18.09 (3.45) | Community | 15.67 (4.40) |
| Interpersonal Relationships | 15.50 (3.63) | Play and Leisure Time | 12.67 (5.48) |
| Coping Skills | 17.33 (3.23) | | |

*DS amyloid burden as measured during analysis; negative includes one subject at or just below threshold depending upon the reference region applied Subject Selection Twelve non-demented adult individuals diagnosed with DS, age 32-61 years, were enrolled in the study. Exclusion of a diagnosis of dementia was based on absence of evidence of recent deterioration in cognitive function found not secondary to medical illness (e.g. hypothyroidism, sleep apnea) or mental illness (e.g. depression), in conjunction with absence of a significant decline in function over a period of six months or more. The diagnosing neurologist was experienced with premorbid deficits in DS and incorporated dementia diagnosis recommendations from the National Task Group on Intellectual Disabilities and Dementia Practices. Ten subjects were female and six were ApoE e4 carriers. All assessments were conducted by UCSD in collaboration with the ADCS under IRB-approved protocols with patient informed consent. Subject demographics are shown in Table 1, including comparator subjects described below.

Image Data Acquisition, Processing, and Analysis

All subjects received FDG PET, florbetapir (amyloid) PET, and structural MRI (sMRI) scans, acquired and processed as described in supplemental material. Image analysis consisted of three parallel, complementary approaches as described below. All FDG PET and MRI analyses were performed while blinded to amyloid, ApoE e4, and clinical status. Each DS FDG PET scan was scored using a pre-defined AD Progression Classifier. This classifier, previously developed using machine learning and 166 subjects from the Alzheimer's Disease Neuroimaging Initiative characterized by clinical diagnosis, amyloid status, and longitudinal outcome, assigned a numeric canonical variate ("CV") score reflecting the degree to which the subject's scan expresses a pattern of relative hypo- and hyper-metabolism associated with AD progression. DS CV scores were then compared to mean scores previously derived from ADNI subjects at stages from amyloid negative ("Am−") normal ("NL") to amyloid positive ("Am+") AD.

Separately, voxel-based, multivariate analysis software was applied to identify patterns in FDG PET and T1-weighted sMRI characterizing similarities and differences between the DS group and pre-defined comparator groups. Four sets of 12 subjects each from the ADNI database (for balanced N) were identified a priori based on ADNI clinical diagnosis, amyloid status, and age: (1) Am− NL, (2) Am+ AD, (3) Am+ early MCI ("EMCI"), and (4) Am+ late MCI ("LMCI"). Since the DS FDG and MRI scans were acquired using ADNI protocols, it was possible to use ADNI subjects whose scans we had previously processed. Subjects were considered Am− if cerebrospinal fluid ("CSF") Abeta42 was >209 or their amyloid scan was negative (11C-PiB threshold 1.47, florbetapir standardized uptake value ratios ("SUVr")<1.11), and Am+ if their CSF Abeta42 was <192 or their florbetapir SUVr was ≥1.11.

Given the relatively young age of the DS subjects, the youngest ADNI subjects meeting diagnostic and amyloid criteria were selected.

For analysis, the NPAIRS software package was applied, which uses principal component analysis, canonical variates analysis, and the NPAIRS iterative resampling method to produce an optimized, robust consensus classifier, or set of spatial patterns, that, when mathematically combined, optimally discriminate the classes. Three models (sets of classes) were explored using FDG PET, and the first was also explored using MRI: (1) DS, NL, AD; (2) DS, NL, AD, EMCI, LMCI; and (3) DS, NL. For each model of N classes, N−1 patterns and CV scores were produced to quantify expression of each pattern.

Because ADNI subjects were older than most DS subjects, twelve closely age-matched, Am−, cognitively Normal subjects ("AE-NL") with FDG PET scans were selected for additional comparison in a model of DS, NL, AD, and NL-AE. The purpose was to determine whether differences between DS and NL were consistent with that between DS and AE-NL. Acquisition parameters for these subjects were consistent with ADNI, and their processing parameters were sufficiently similar to enable confirmatory comparison. Due to other processing differences, they were not used as primary comparators.

A priori AD-relevant regions of interest ("ROIs") were measured on the FDG scans, and SUVRs were calculated. Regions included inferior parietal cortex ("IPL"), posterior cingulate-precuneus ("PCC"), hippocampus ("HIP"), medial temporal gyrus ("MTL"; including hippocampus), lateral temporal cortex ("LTL"), middle frontal gyrus ("MFG"), prefrontal cortex ("PFC"), pons as reference region, and gray cerebellum. SUVRs were compared to those for the same regions previously measured on the ADNI comparator subjects.

Once unblinded to amyloid data, each DS subject's amyloid cortical average SUVR was measured by averaging anterior cingulate, posterior cingulate, precuneus, lateral temporal, frontal, and inferior parietal regions, referenced to whole cerebellum.

Statistical Analyses

Each NPAIRS analysis, through iterative resampling, generated measures of reproducibility and predictive power indicating whether results were generalizable. Descriptive statistics were generated for CV score comparisons. FDG PET ROI values were compared using t-test statistics, with and without age correction, between Am− DS, Am+ DS, NL, AD, and AE-NL (divided into younger ("AEy") and older ("AEo") halves). Correlation coefficients (Pearsons R) were measured for FDG AD Progression scores, FDG-CV scores, and sMRI-CV scores vs. age, amyloid SUVR, and baseline clinical measures; amyloid SUVRs vs. baseline clinical measures; and sMRI-CV2 scores vs. FDG AD Progression scores and FDG CV1.2 scores.

Image Data Acquisition

FDG PET images were acquired for all DS subjects on a 2001 Siemens ECAT Exact HR+ scanner (CTI, Knoxville, Tenn.) having a 15.5 cm field of view and 4 mm in-plane spat. The ADNI-2 FDG protocol (ADNI-2 PET Technical Procedures Manual, v1.0, 2011) was followed for data acquisition and reconstruction. For FDG PET, subjects' blood glucose was checked prior to scanning to ensure<180 mg/dL. After the injection of 5 mCi of 18F-FDG, subjects were kept in a quiet, dimly lit room with eyes and ears unoccluded for 30 min, after which they were placed in the PET scanner. Data was acquired in six 5 minute frames, 3D mode, in 63 slices, followed by a 7 minute transmission scan. A soft headrest was used during scanning to allow accurate positioning using a low-power neon laser. Reconstruction was performed for all PET scans using OSEM [128×128 matrix, 4i16s, zoom factor of 2, no x or y offsets, brain mode On, Filter all pass, and smoothing Kernel 5.0 mm FWHM, no Axial filtering, Scatter Correction On. A 7 min transmission scan was used for attenuation correction.

For florbetapir data acquisition, subjects received IV injections of 10 mCi of Florbetapir F 18 and, after 40 minutes of uptake, 10 minutes of emission data were collected by the Siemens EXACT HR+ 961 PET tomograph (CTI, Knoxville, Tenn.), which yielded 63 transverse sections spaced 2.43 3.5 mm apart with a 15.5-cm field of view (FOV) in 3D mode, with 4-mm in-plane spatial resolution (FWHM). Each subject was placed in a headholder during scanning to allow accurate positioning using a low-power neon laser. Images were acquired at an angle parallel to the cantho-meatal plane and reconstructed using a Hann filter (cut-off frequency=0.5 cycles/pixel) into 128×128 pixel images.

The MRI protocol included series to assess for structural pathology (T2-weighted fluid attenuated inversion recovery, T2*-weighted gradient recalled echo, and diffusion weighted imaging) along with a series modeled on the non-accelerated T1-weighted sequence from ADNI for volumetric processing (3D inversion recovery prepared spoiled gradient recalled imaging; inversion time 500, flip angle 10, 1.25 mm×1.25 mm in-plane resolution, 156 sagittal slices with 1.2 mm spacing). Scanning was performed on a 1.5 Tesla GE Signa HDxt scanner, and radiologist overread was performed on all scans to identify any clinically significant incidental findings. All scans were uploaded to the ADCS study data portal. The ADCS Imaging Core reviewed review each uploaded scan and confirmed whether any re-processing was needed.

Image Data Processing

The FDG PET and MR images and age and gender information for each of the 12 subjects were provided to ADM Diagnostics LLC (ADMdx) for analysis blinded to amyloid status, ApoE e4 genotype, clinical, or other measures. In order to apply the AD Progression Classifier and also to enable comparison to ADNI images, the FDG PET images were co-registered to a PET-derived template that had been co-registered to a fully pre-processed exemplar from ADNI to ensure correct orientation, slice thickness, and bounding box dimensions. A whole brain binary mask was derived from this modified template, which was applied to intensity normalize (scale) each image to a mean value of 1.0. Scans were smoothed to the ADNI standard resolution. The DS subject and ADNI comparator images were then spatially normalized to a customized FDG-PET template in MNI space using AIR.

The subjects' amyloid PET scans, provided to ADMdx after the blinded analysis of FDG PET data, were co-registered with their respective MRI scans, which were segmented into gray, white, and CSF tissue using SPM8 (The Wellcome Trust Centre for Neuroimaging, UK). A set of pre-defined template volumes of interest ("VOIs") including frontal, anterior cingulate, posterior cingulate, precuneus, lateral temporal, parietal cortex, and whole cerebellum was transformed using to the native scan of each subject through application of the spatial transformation. Cortical regions were masked using the thresholded gray segment of each subject's co-registered MRI. A cortical average SUVR was calculated as the average of the six target regions divided by the whole cerebellum value. Amyoid status was also examined by visual inspection. The FDG PET and ADNI comparable scans were processed in the same manner to enable measurement of VOIs in native space. For FDG, measured ROIs included posterior cingulate, precuneus, anterior cingulate, prefrontal cortex, hippocampus, medial temporal cortex (including hippocampus), cerebellum, and pons. Image processing was performed using PETMAX™ software (ADM Diagnostics LLC, Chicago, Ill.), a software platform optimized for clinical trials that enables extensive visual and automated quality control and automated processing with audit trail.

In addition, the MRIs were spatially normalized to a common template using VBM8. Modulated gray segments were produced with application of Jacobian modulation to restore absolute gray matter volumes and normalized to total intracranial volume, and smoothed by a three dimensional Gaussian filter of 8 mm kernel size.

NPAIRS Multivariate Analysis

Machine learning approaches that employ multivariate approaches can far outperform univariate methods because they take into account relationships between voxels, which are highly correlated in diseases such as AD. In addition, they enable identification of the relative contributions of different, uncorrelated networks to the overall variance across classes. However, multivariate machine learning classifiers can be prone to overfitting, reducing generalizability. Herein, stable, generalizable results were accomplished by applying canonical variates analysis (CVA; a linear discriminant method) after dimensionality reduction using principal component analysis ("PCA"). The model was developed within the NPAIRS (Nonparametric, Prediction, Activation, Influence, Reproducibility, reSampling) analysis framework, which uses split-half resampling for simultaneous determination and optimization of prediction and reproducibility. Data sets were repeatedly subdivided into training and validation sets, by which NPAIRS produced a robust consensus classifier with prediction and reproducibility metrics of the discriminant pattern for optimization. The resulting classifier included a set of mathematically related spatial patterns that together describe the variance across classes. A numeric CV score quantified the degree to which each subject expresses each given pattern relative to other subjects.

Results

Amyloid Status

Three DS subjects were Am− as measured using florbetapir PET, one was at threshold, and eight were Am+. Of Am− or threshold DS subjects, three were ApoE 3/3, and one was 2/4. Five (62%) of the Am+ subjects were heterozygous (3/4) ApoE e4 carriers and three were non-carriers.

FDG AD Progression Classifier Scores

DS AD Progression scores (FIG. 6A) ranged from values typical of Am− NL subjects to those of subjects with AD as established through previous independent testing of ADNI subjects of known clinical diagnosis and amyloid status. AD Progression scores increased with increasing age ($R^2=0.39$, $p<0.05$) and with amyloid burden. All Am− or threshold subjects had scores reflecting less AD-like pattern expression than that typical of late MCI or AD.

FDG NPAIRS Comparisons

Figure 5A:
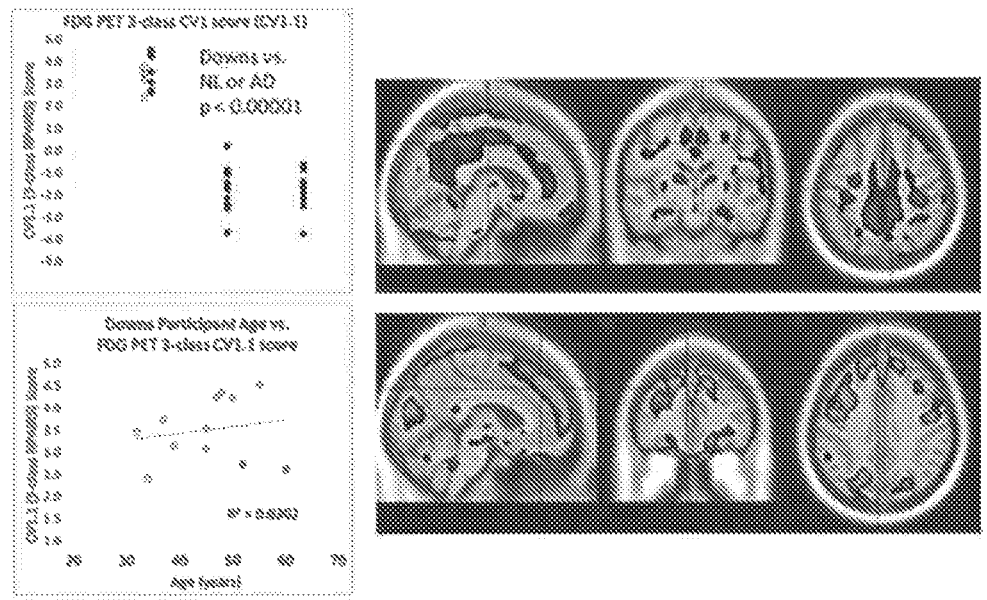
FIG. 5A is a graphical illustration showing Down's Syndrome ("DS")-specific and AD-specific patterns derived from FDG PET images.
Figure 5B:
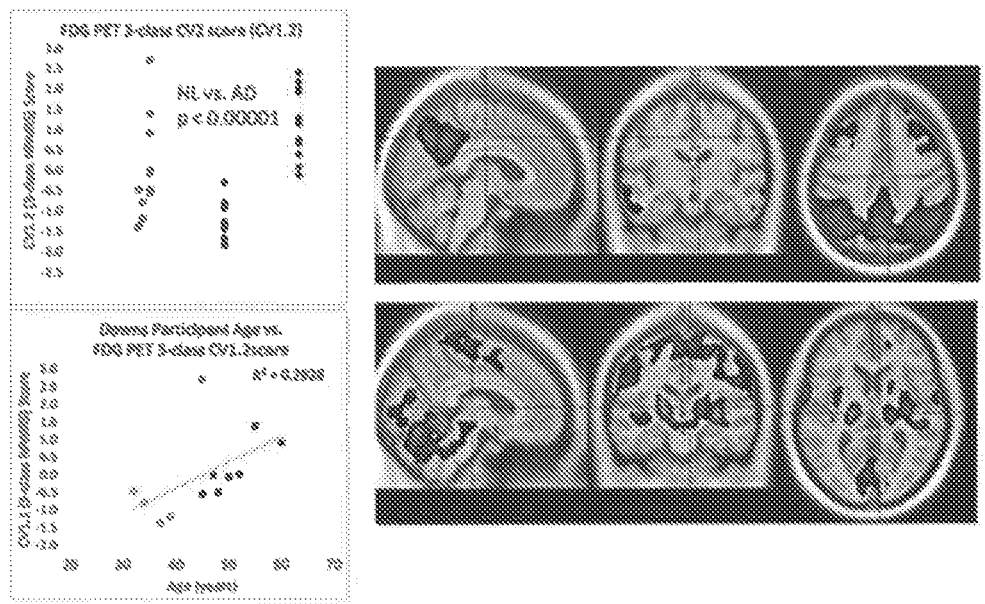
FIG. 5B is another graphical illustration showing Down's Syndrome ("DS")-specific and AD-specific patterns derived from FDG PET images.

Results of the NPAIRS 3-class comparison of DS, NL, and AD are shown in FIG. 5. Two distinct glucose metabolism patterns with partial overlap were identified, each having reproducibility and prediction metrics indicating generalizability to a broader population (as did all patterns discussed). The first pattern (FIG. 5A, CV1.1) differentiated DS from NL and AD ($p<0.00001$), whereas the second (FIG. 5B, CV1.2) separated NL from AD ($p<0.00001$). Pattern features are relative to brain mean; therefore hypermetabolism or volume increases can also be interpreted as relative preservation.

In the DS-associated pattern CV1.1, hypometabolism was observed in posterior cingulate, anterior cingulate, precuneus (particularly anterior), paracentral lobule, postcentral gyrus/supplementary motor cortex, superior temporal cortex, hippocampus, striatum, insula, and inferior frontal cortex. Relative hypermetabolism was found in frontal cortex, superior temporal gyrus, and occipital cortex. There was no separation between Am− and Am+ DS subjects (CV1.1 plot, FIG. 5A). This pattern did not correlate with age.

The second pattern (CV1.2, FIG. 5B) distinguished NL from AD ($p<0.00001$), characterized by hypometabolism in posterior cingulate, posterior precuneus, inferior parietal cortex, lateral temporal cortex, and prefrontal cortex. Relative hypermetabolism was found in cerebellum, pons, paracentral lobule, putamen, thalamus, and occipital subregions. DS scores distributed across the range from NL to AD. All Am− or threshold subjects had CV1.2 scores in the range of NL. CV1.2 correlated with age in DS subjects ($R^2=0.29$, $p<0.07$).

Figure 6:
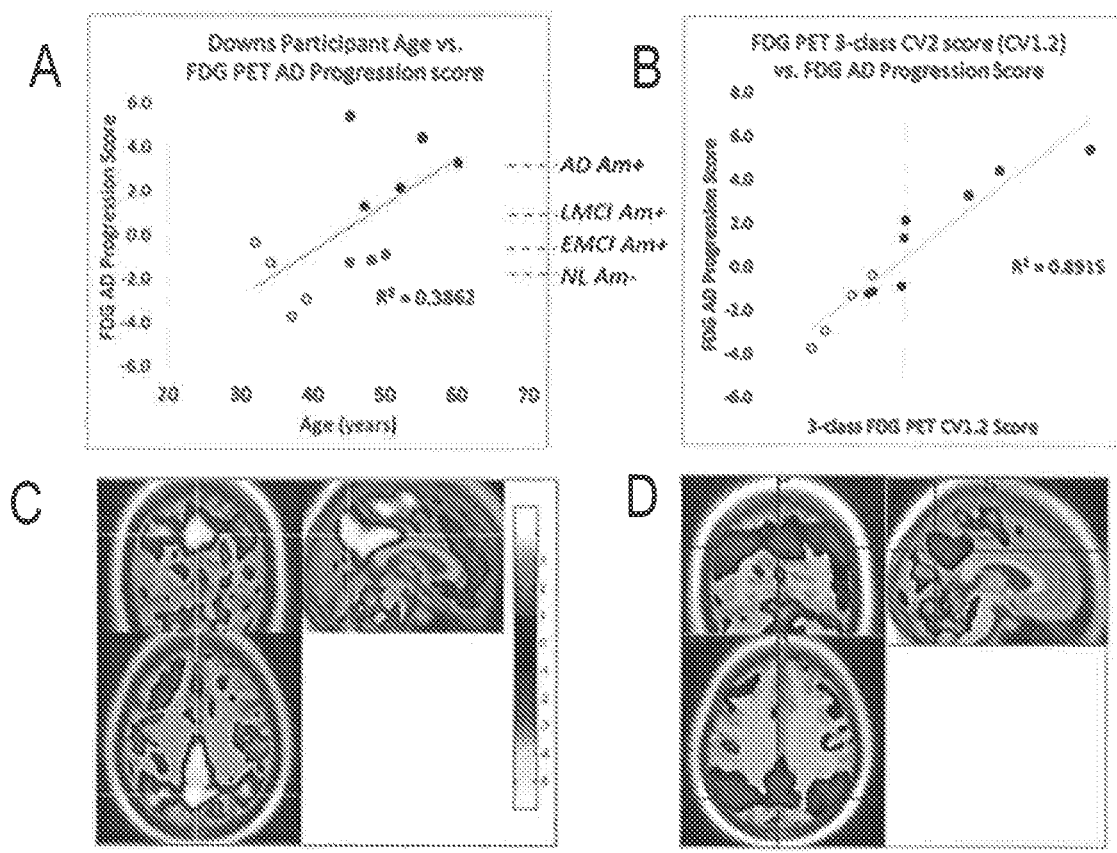
FIG. 6 is a graphical illustration showing AD progression scores of DS subjects, and correlation with age.

In FIGS. 6B and 6D the CV1.2 scores correlated with FDG AD Progression scores ($R^2=0.89$, $p<0.00001$), and the pattern was highly similar to the apriori AD Progression pattern (FIG. 6C, 6D), dominated by hypometabolism in posterior cingulate, precuneus, and inferior parietal cortices with preservation in cerebellum, pons, paracentral lobule, thalamus, and striatum.

Results of the 5-class NPAIRS analysis of DS, NL, EMCI, LMCI, and AD subjects provided a finer resolution comparison of DS subjects to the AD progression spectrum. The 5-class CV1 pattern was similar to CV1.1, differentiating DS from all other groups ($p<0.00001$), and with no differentiation between non-DS groups. An AD-like CV2 pattern showed cascade-like progression from NL to EMCI to LMCI to AD as found in the apriori AD Progression classifier, with DS subjects scoring across the spectrum from NL to AD as in the 3-class comparison.

Providing confirmation that the DS-associated pattern CV1.1 was not attributable to DS vs. ADNI subject age differences, the NPAIRS analysis of DS, NL, AD, and AE-NL subjects produced a CV1 pattern differentiating DS similarly from NL and AE-NL, and highly similar to CV1.1.

Demonstrating the limitations of a 2-class analysis, as well as its relationship to the multi-pattern models, the comparison of DS and NL subjects-only produced a single pattern differentiating DS and NL. The pattern incorporated elements from both CV1.1 and CV1.2 patterns, but similar to published studies, the contributing effects of DS and AD could not be dissociated.

TABLE 2

Region of interest value comparisons, referenced to pons.

| | p-values | IPL | PCC | HIP | MTL | LTL | PFC | MFG |
|---|---|---|---|---|---|---|---|---|
| a | NL < AM-NL | 0.11 | n.s. | 0.15 | <0.0001 | n.s. | n.s. | n.s. |
| b | AD < NL | <0.0001 | <0.0001 | 0.01 | 0.008 | <0.0001 | 0.003 | 0.0003 |
| c | AD < Am− DS | <0.0001 | 0.02 | n.s. | n.s. | 0.001 | 0.02 | 0.001 |
| d | AD < Am+ DS | n.s. | n.s. | 0.10 | n.s. | n.s. | n.s. | n.s. |
| e | Am− DS < NL | n.s. | 0.06 | 0.001 | 0.02 | n.s. | n.s. | n.s. |
| f | Am− DS < AMy-NL | 0.03 | 0.02 | 0.01 | 0.0009 | n.s. | 0.12 | 0.06 |
| g | Am+ DS < NL | 0.002 | 0.0004 | <0.0001 | 0.001 | 0.001 | 0.002 | 0.008 |
| h | Am+ DS < AMo-NL | 0.004 | 0.002 | <0.0001 | <0.0001 | 0.04 | 0.02 | 0.03 |
| i | Am+ DS < Am-DS | 0.02 | 0.05 | 0.04 | 0.05 | 0.02 | 0.02 | 0.03 |

FDG Region of Interest Analysis Results

NL and AE-NL groups differed only in MTL, with trend differences in HIP and IPL (Table 2a). Glucose metabolism relative to pons was lower in AD vs. NL in all regions evaluated. There were no significant differences between the Am+ DS subjects vs. AD in any region except HIP, where Am+ DS had more-pronounced hypometabolism than AD (trend). Although the group size of Am− or threshold DS subjects (N=4) was below that needed for a conclusive t-test, an exploratory non-parametric t-test suggested that AD subjects had lower metabolism than Am− DS in IPL, PCC, LTL, PFC, and MFG, but similar in HIP and MTL. Am− DS had lower metabolism in HIP, MTL, and PCC relative to NL, and in IPL relative to AEy-NL. Am+ DS were hypometabolic in all regions compared to NL and AEo-NL groups and Am− DS. Am− and Am+ DS had lower cerebellar metabolism than NL; Am+ DS were lower than NL, Am− DS, and AD ($p<0.0001$). Age-corrected and uncorrected results were similar.

Figure 7A:
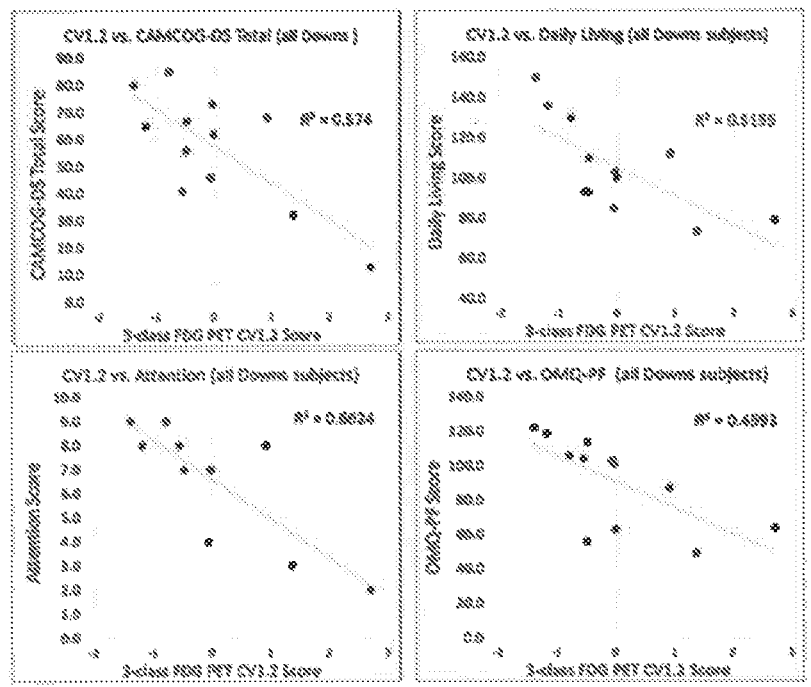
FIG. 7A is a graphical illustration showing correlations between CV1.2 score in DS subjects vs cognitive and functional measures at baseline, and amyloid SUVR in DS subjects versus cognitive and functional measures at baseline.
Figure 7B:
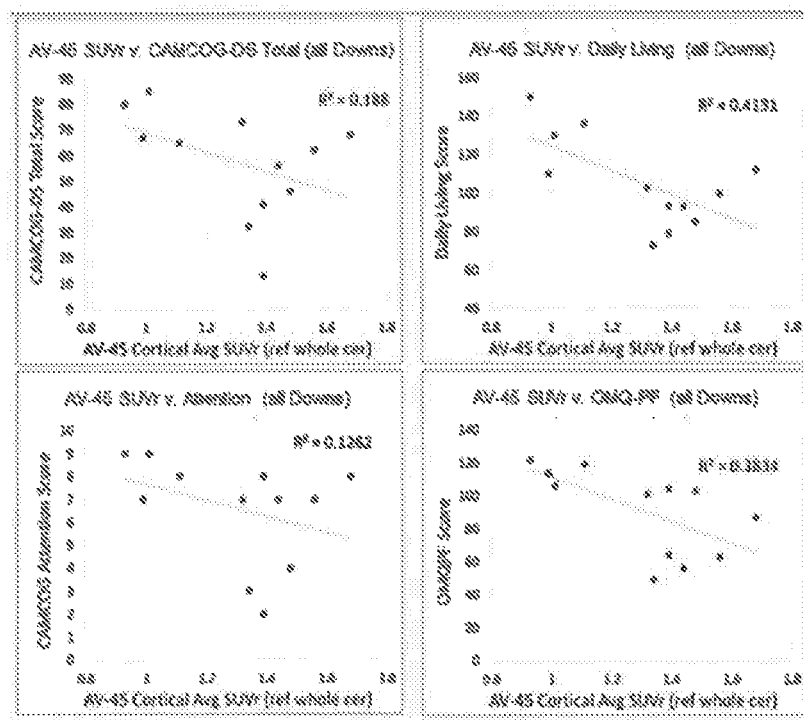
FIG. 7B is a graphical illustration showing correlations between CV1.2 score in DS subjects vs cognitive and functional measures at baseline, and amyloid SUVR in DS subjects versus cognitive and functional measures at baseline.
Figure 8A:
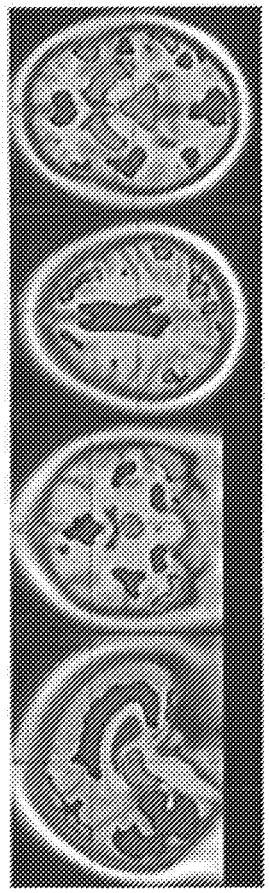
FIG. 8A is a graphical illustration showing DS specific and AD-related structural magnetic resonance imaging ("sMRI") patterns derived from an MRI 3-class analysis.
Figure 8A:
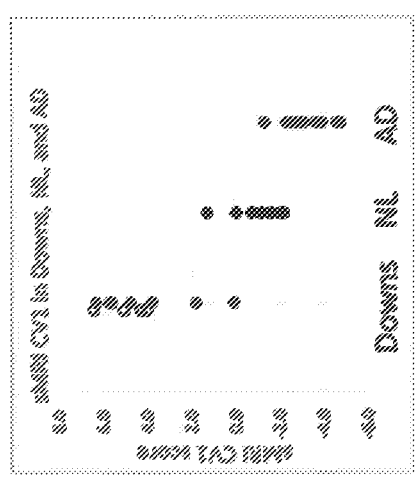
Figure 8B:
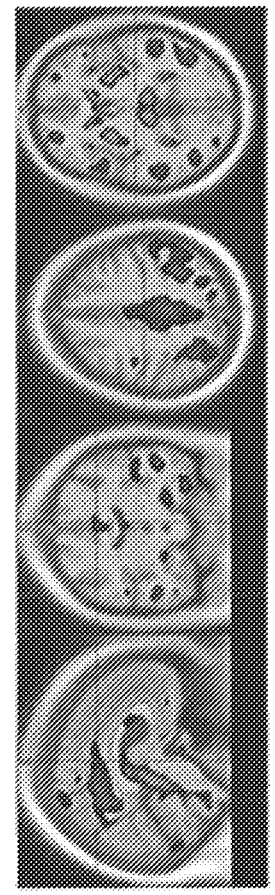
FIG. 8B is another graphical illustration showing DS specific and AD-related structural magnetic resonance imaging ("sMRI") patterns derived from an MRI 3-class analysis.
Figure 8B:
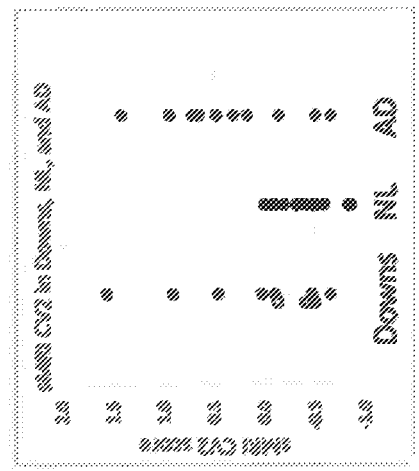

Correlation Between FDG and Amyloid PET Markers and Cognitive/Functional Measures In FIG. 7 correlations between CV1.2 score in Downs subjects vs cognitive and functional measures at baseline, and amyloid SUVR in Downs subjects versus cognitive and functional measures at baseline are shown. CV1.2 score correlated with several baseline clinical measures in DS subjects, including Total Memory ($p<0.01$), Language ($p<0.02$), Attention ($p<0.001$), Total Score 2 (composite of Orientation, Language, Remote Memory, Recent Memory, Attention, Abstraction, Perception, $p<0.004$), Daily Living Skills ($p<0.01$), and Observer Memory Questionnaire-Parent Form (OMQ-PF; $p<0.01$) (FIG. 7A). In contrast, while Am− status corresponded to better cognitive and functional scores than Am+ status, there was no correlation between amyloid SUVR and clinical endpoints within the Am+ subset (FIG. 7B).

Structural MRI (sMRI) Results

In FIG. 8 results from the 3-class NPAIRS analysis of the modulated gray MRI segments of DS, NL, and AD are shown, which produced two CVs. The first CV (sMRI-CV1) differentiated DS from NL ($p<0.00001$) and AD ($p<0.00001$), and less so discriminated NL and AD (FIG. 8A). This pattern showed DS volume reductions in cerebellum, occipital cortex, hippocampus, mid-cingulate, anterior cingulate, and temporal cortex. Preserved or increased volume was found in DS in caudate, putamen, thalamus, inferior lateral temporal cortex, inferior parietal cortex, and prefrontal cortex compared to NL and AD. AD scores were lower than NL, to interpret in combination with sMRI-CV2. The second CV (sMRI-CV2) differentiated AD and NL ($p<0.0005$), whereas DS scores distributed across the range from NL to AD. This pattern showed volume reductions in posterior cingulate, precuneus, parietal cortex, hippocampus, temporal cortex, frontal cortex, and caudate, with preserved or increased volume in putamen, thalamus, and midbrain. Volume reductions were consistent with AD-like atrophy. As in FDG CV1.1, there was no association between sMRI-CV1 score and amyloid status or age in DS subjects. As in FDG CV1.2, four of six subjects with the lowest sMRI-CV2 scores were Am− or threshold.

Noteworthy, some scans had motion artifacts that introduced noise into the analyses. One scan was excluded from analyses in FIG. 8 and FIG. 9 due to blurring effects. Three Am+ DS subjects showed notable ventricular enlargement.

Figure 9A:
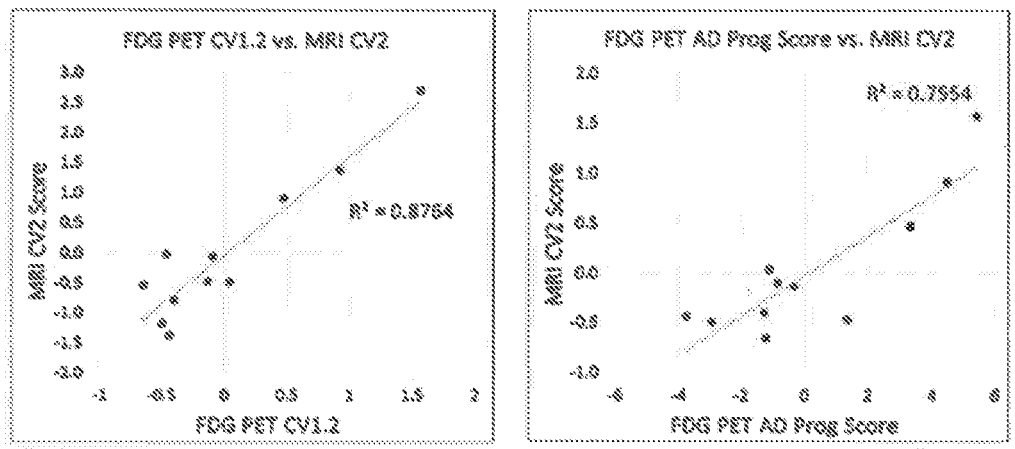
FIG. 9A is a graphical illustration showing correlations between functional and structural patterns.
Figure 9B:
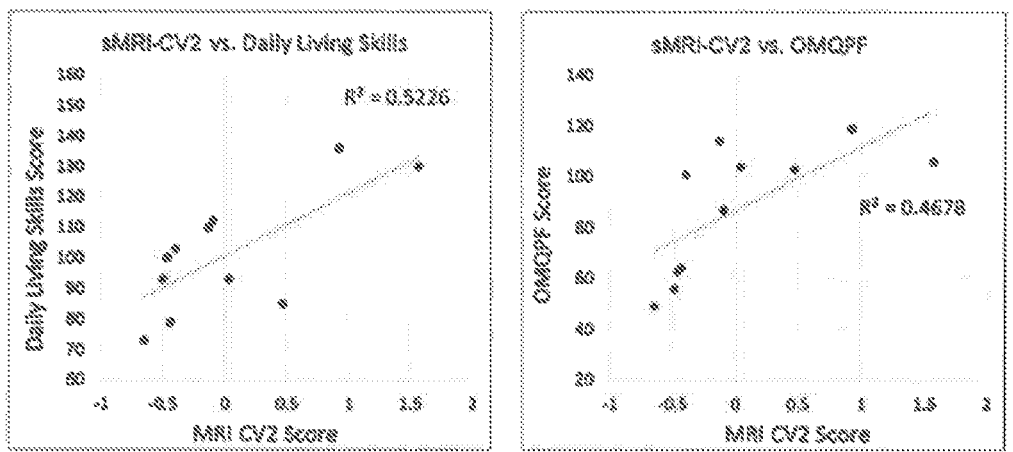
FIG. 9B is another graphical illustration showing correlations between functional and structural patterns.

The DS sMRI CV scores showed weaker relationships with clinical measures than FDG CV scores. The sMRI-CV1 scores correlated ($p<0.05$) with Delayed Memory, Daily Living Skills, and Socialization; sMRI-CV2 correlated ($p<0.05$) with Delayed Memory, Total Score 1, Daily Living Skills, Socialization, and OMQ-PF. The sMRI-CV2 score correlated with FDG CV1.2 ($R^2=0.89$, $p<0.00002$) and AD Progression Score ($R^2=0.76$, $p<0.0007$) (FIG. 9).

Conjunction of Functional and Structural Results

Structural pattern sMRI-CV2 correlated with FDG CV1.2 and AD Progression scores ($R^2=0.88$, 0.76; FIG. 9). Common regions between FDG CV1.1 and sMRI-CV1 included relative hypometabolism and volume reduction in mid-cingulate, anterior cingulate, paracentral lobule, and hippocampus; relative hypermetabolism and volume preservation in prefrontal cortex; and relative hypermetabolism but volume reduction in occipital cortex. Common regions between FDG CV1.2 and sMRI-CV2 included relative hypometabolism and reduced volume in posterior cingulate, precuneus, inferior parietal cortex, and hippocampus; and relative hypermetabolism and volume preservation in putamen and thalamus.

There were some differences between the FDG and sMRI findings. Cerebellar volume reduction was seen in DS compared to NL and AD, but metabolic differences were subtle. Volume preservation in thalamus, striatum, and lateral inferior temporal cortex were found in DS compared to NL, but metabolic differences were not observed within CV1.1. Medial frontal hypermetabolism was found in DS relative to NL and AD, but without volumetric preservation.

Discussion

In this study, within-subject dissociation of functional and structural effects of DS from those due to progressing AD were demonstrated. Results showed that the degree of Alzheimer's-type neurodegeneration, reflected in FDG and MRI biomarkers, can be quantified in non-demented DS subjects. The findings show that AD pattern expression varies greatly within Am+ DS subjects, as do clinical symptoms, consistent with variability found among Am+ persons without DS, and underscoring the importance of characterization. It was found that both functional and structural CV scores correlated with cognitive and functional endpoints.

The DS-specific FDG CV1.1 pattern hypometabolism partially overlapped but was distinct from the AD-like CV1.2 pattern. Shared posterior cingulate hypometabolism was consistent with that found in non-demented DS and to a greater extent in demented DS previously. Hypometabolism in paracentral lobule and striatum and the prominent anterior cingulate and inferior frontal regions (less dominant in the AD pattern), differed from core AD features. The mid- and anterior cingulate regions of CV1.1 have been associated with motor activation, error detection, and emotion. It was unclear whether the hypometabolism in posterior cingulate and hippocampus in CV1.1 reflected early, "baseline" predisposition to AD as found in young, presymptomatic ApoE e4 carriers. Regardless, these alterations were present even in Am− DS subjects in this study, distinct from amyloid burden. In the 5-class analysis, DS subjects differed equally in the Down-specific CV from all classes along the AD progression path. This differs from findings that Am+ NL (at earliest stages of disease) position between Am− NL and Am+ EMCI in AD-like pattern expression, and supports a DS, rather than AD, effect.

The relative frontal hypermetabolism within CV1.1 was consistent with reports of regional hypermetabolism in young DS subjects. In such studies, compensatory activity in response to deficient neural networks was hypothesized, and/or a lower effectiveness of glycolysis related to down-regulation of phosphoglucose isomerase, elevating glucose-6-phosphate.

The AD-like FDG pattern (CV1.2) was consistent with present FDG AD Progression pattern and AD literature, supporting AD-relevance and robustness despite small sample size. As in ADNI subjects, the AD-like pattern in DS subjects correlated with clinical endpoints. Medial temporal hypometabolism was present in CV1.2 at lower thresholds. HIP and PCC ROI hypometabolism were identified in Am− and Am+ DS subjects compared to NL (more prominent in Am+ DS). This suggests an additive effect in these regions as DS becomes confounded by AD. The presence of AD-like effects in non-demented DS was consistent with previous findings of an AD-like pattern in older non-demented DS.

DS-specific pattern sMRI-CV1 was consistent with reports of reduced cerebellar, cingulate, and hippocampal volume but preserved or increased subcortical volume, while sMRI-CV2 was consistent with AD-related atrophy.

FDG and sMRI findings showed similarities and differences in the patterns differentiating DS from Normal patients. Of note is the cerebellum, which is involved in motor and postural control, affected in DS. Despite reduced cerebellar volume in DS compared to NL, cerebellar hypometabolism was subtle, significant only in Am+ DS. Relevant DS mouse model work found that despite reduced volume and cell density, there were no synaptic plasticity deficits to which motor deficits could be attributed. The present findings show that information provided by structural and functional imaging may be complementary. Limitations included small sample size and motion artifact in some scans; however, results demonstrated a strength of the present approach in handling subject-related noise. Although age effect was not observed in the DS-specific patterns, studying younger adults may help to resolve the contrast between hypometabolism observed in subjects studied herein, and the hypermetabolism-only findings of some studies in young subjects.

As appreciated from above, the ability to dissociate functional and structural effects arising from AD vs. DS, and to quantify degree of AD progression, has potentially profound value for clinical trials of AD-targeted therapies in DS adults, including enabling identification of subjects likely to progress within a trial, and detection of disease-specific treatment response.

Example II

Using methods as described herein, a five class multivariate NPAIRS analysis was performed to evaluate possible difference in volumetric effects for patients with Down Syndrome ("DS") versus those of Alzheimer's Disease ("AD") using longitudinal MRI and 2-year Tau image data. The groups included 12 Normal Am− subjects from ADNI, 12 AD Am+ subjects from ADNI (12 subjects), 9 DS subjects at baseline (Year 0), as well as Year 1 and Year 2 from baseline. DP04 did not have longitudinal follow up and was excluded. DP03 had excessive motion and blur, and was excluded. DP12 has ring artifact suggesting motion and was excluded.

Figure 10:
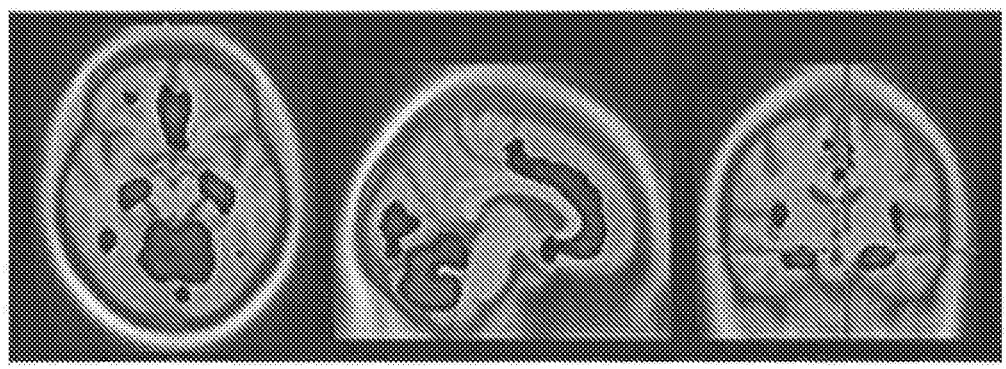
FIG. 10 is a graphical illustration CV1 patterns and scores for normal AD, and DS patients tracked over a period of time.
Figure 10:
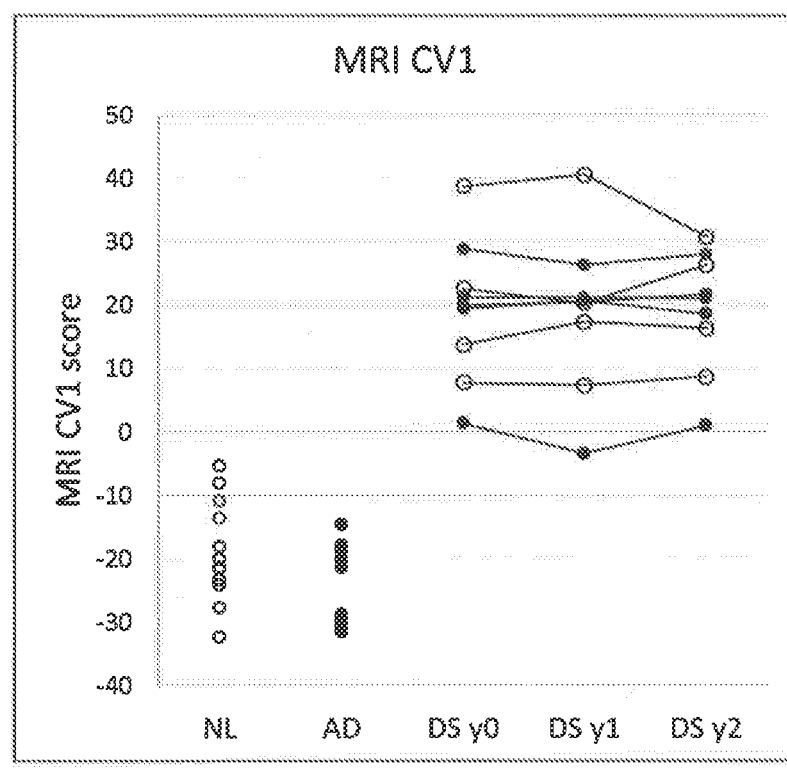

The analysis produced two Canonical Variate (CV) patterns, as in previous analysis of baseline scans. The first (CV1) was associated with DS independent of amyloid status, and this pattern was longitudinally stable, as illustrated in FIG. 10. The higher a subject's score, the more they expressed the pattern of reduced volume relative to low scoring subjects. In FIG. 10, unfilled circles represent amyloid negative or threshold, and unfilled triangles represent amyloid positive but tau negative. For the DS subjects, filled circles represent Am+ and Tau+, AD filled circles represent Am+ and likely Tau+.

Figure 11:
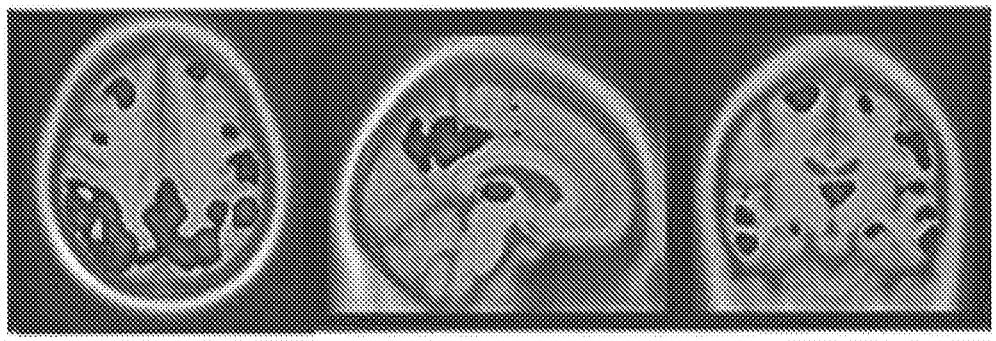
FIG. 11 is a graphical illustration CV2 patterns and scores for normal AD, and DS patients tracked over a period of time.
Figure 11:
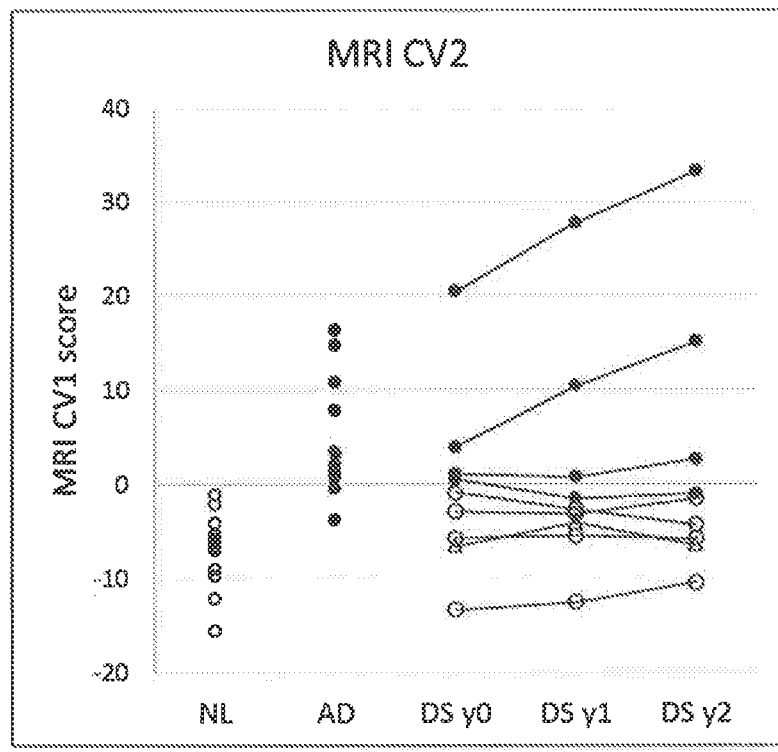

The second (CV2) was associated with the differentiation of NL Am− vs. AD Am+ and progressed in some DS subjects, notably those who were Am+ Tau+, as illustrated in FIG. 11. Specifically, CV1 differentiated NL subjects AD, and DS subjects showed scores across the spectrum from NL to AD levels. Am+ DS subjects had greater scores than Am− DS subjects and one Am+ Tau− DS subject. While the majority of Am− subjects did not progress, Am+ Tau+ subjects showed progression with regard to this pattern at varying rates. In FIG. 11, unfilled circles represent amyloid negative or threshold, unfilled triangle represent amyloid positive but tau negative. For DS subjects, filled circles represent Am+ and Tau+, AD filled circles represent Am+ and likely Tau+.

Patterns differentiating adult DS subjects from NL or AD subjects are shown to be disassociated from patterns of AD progression using a multivariate machine learning. In addition, the DS specific pattern (CV1) was stable longitudinally (2 year period). The AD-like pattern (CV2) was progressive to different extents in Am+DS subjects, and in general did not show progression in Am− DS subjects or the Am+ Tau− DS subject.

As appreciated from these results, patterns of structural change attributable to progressive AD in comparison to DS may enable evaluation of longitudinal disease progression and disease-specific drug effect. In particular, it was shown that an MRI DS pattern can remain stable over time whereas an MRI AD pattern showed progression (an increase in numeric score corresponding to Alzheimer's disease pattern expression) specifically in those subjects who had accumulated amyloid plaque and tau.

In summary, the present disclosure describes systems and methods for identifying the brain condition of a patient subject to a plurality of disease states. Although applied in the context to brain disorders, it is envisioned that the present approach can be extended to a wide range of applications. In addition, the present approach can be applied to any set of conditions, where each condition is associated with a "signature pattern" of image and/or other data, which may be a set of cognitive, lab, demographic, genotype or other performance data. By identifying a population that may have one or more disorders, and comparing to known disorders, a new pattern or signature of data that characterizes the "unknown" disorder may be identified, as well as the ability to identify and track the contribution of each disorder.

For example, marketing and product/service companies aim to characterize specific product or service targets. These may range from food providers to hair/cosmetic products to recreational items to hotel and vacation services. They may have a set of data (which may include demographics, buying history, personal preferences, income, or other data) characterizing a population that is attracted to A and B, and data characterizing a population that is attracted specifically to B. However, they may not know what characterizes the population specifically attracted to A. Alternatively, in the context of insurance and risk assessment, they may have a set of data characterizing people who develop one problem ("problem B"), a set of data characterizing people who do not develop any problems, and a set of data characterizing people who develop a combination of two problems ("problems A and B"). They wish to identify who is likely to develop problem A, specifically. In all of these broader cases, the approach described herein could be readily applied.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for identifying a brain condition of a patient subject to a plurality of disease states, the method comprising:
   a) receiving imaging data associated with a patient's brain acquired using an imaging system, each image of the imaging data expressing the plurality of disease states, the plurality of disease states including at least first and second co-morbid disease states;
   b) constructing a classifier having signatures corresponding to the plurality of disease states;
   c) applying the classifier to the imaging data to determine a degree to which the patient expresses at least one of the plurality of disease states;
   d) determining a brain condition of the patient using the determined degree; and
   e) generating a report indicative of the brain condition of the patient.

2. The method of claim 1, the method further comprising constructing the classifier using a machine learning algorithm.

3. The method of claim 1, wherein applying the classifier includes comparing the imaging data to at least one signature to determine the degree to which the patient expresses at least one of the plurality of disease states.

4. The method of claim 1, the method further comprising separating the imaging data according to the degree to which the patient expresses the at least one of the plurality of disease states.

5. The method of claim 1, the method further comprising determining a future disease state of the patient using the brain condition determined at step d).

6. The method of claim 1, the method further comprising determining an effectiveness of a treatment using the brain condition determined at step d).

7. A method for identifying a brain condition of a patient subject to a plurality of disease states, the method comprising:
   a) acquiring imaging data associated with a patient's brain, each image of the imaging data expressing the plurality of disease states, the plurality of disease states including at least first and second co-morbid disease states;
   b) applying a classifier to the imaging data to determine a degree to which the patient expresses at least one of the plurality of disease states;
   c) separating the imaging data using the determined degree to produce datasets corresponding to the at least one of the plurality of disease states;
   d) determining a brain condition of the patient using respective datasets; and
   e) generating a report indicative of the brain condition of the patient.

8. The method of claim 7, wherein the imaging data includes at least one of a Positron Emission Tomography ("PET") data, a Computed Tomography ("CT") data, a Magnetic Resonance Imaging ("MRI") data, or a Single Photon Emission Computed Tomography ("SPECT") data.

9. The method of claim 7, the method further comprising constructing, using data from one or more patient groups, a classifier having signatures corresponding multiple disease states.

10. The method of claim 9, the method further comprising constructing the classifier using a machine learning algorithm.

11. The method of claim 7, the method further comprising determining a future disease state of the patient using the brain condition determined at step d).

12. The method of claim 7, the method further comprising determining a progression of the brain condition using reference data.

13. The method of claim 12, wherein the reference data is acquired from the patient at a time point prior to the imaging data.

14. A system for identifying a brain condition of a patient subject to a plurality of disease states, the system comprising:
   a processor configured to:
      i) receive image data associated with a patient subject's brain, each image of the image data expressing the plurality of disease states, the plurality of disease states including at least first and second co-morbid disease states;
      ii) construct a classifier having signatures corresponding to a plurality of disease states;
      iii) apply the classifier to the imaging data to determine a degree to which the patient expresses at least one of the plurality of disease states;
      iv) determine a brain condition of the patient using the determined degree; and
      v) generating a report indicative of the brain condition of the patient.

15. The system of claim 14, wherein the imaging data includes Positron Emission Tomography ("PET") data, a Computed Tomography ("CT") data, a Magnetic Resonance Imaging ("MRI") data, or a Single Photon Emission Computed Tomography ("SPECT") data.

16. The system of claim 14, wherein the processor is further configured to construct the classifier using a machine learning algorithm and data from one or more patient groups, the classifier having signatures corresponding multiple disease states.

17. The system of claim 14, wherein the processor is further configured to separate the imaging data using the determined degree to produce datasets corresponding to each of the at least one of the plurality of disease states.

18. The system of claim 14, wherein the processor is further configured to determine a risk for the patient to develop a disease state using the determined brain condition.

19. The system of claim 14, wherein the processor is further configured to determine an effectiveness of a treatment using the brain condition.

20. The system of claim 14, wherein the processor is further configured to determine a progression of the brain condition using reference data acquired at a time point prior to the imaging data.

21. A method for generating a classifier to identify a brain condition of a patient subject to a plurality of disease states, the method comprising:
   a) accessing data parameters acquired from a plurality of patient groups, the data parameters from each patient group expressing the plurality of disease states, the plurality of disease states including at least first and second co-morbid disease states;
   b) assembling the data parameters into a plurality of disease state classes and disease state sub-classes;
   c) generating, using plurality of disease state classes and disease state sub-classes, a classifier having signatures distinguishing the plurality of disease states;
   d) providing the classifier as a reference for identifying a brain condition of a patient subject to at least one of the plurality of disease states.

22. The method of claim 21, wherein the data parameters comprise imaging data including at least one of a Positron Emission Tomography ("PET") data, a Computed Tomography ("CT") data, a Magnetic Resonance Imaging ("MRI") data, or a Single Photon Emission Computed Tomography ("SPECT") data.

23. The method of claim 21, the method further comprising constructing the classifier using a machine learning algorithm.

* * * * *